United States Patent
Bridgewater et al.

(10) Patent No.: US 11,986,502 B2
(45) Date of Patent: May 21, 2024

(54) BACTERIOPHAGE COMPOSITIONS AND KITS AND RELATED METHODS

(71) Applicant: BRIGHAM YOUNG UNIVERSITY, Provo, UT (US)

(72) Inventors: Laura Bridgewater, North Provo, UT (US); Gongze Zhao, Highland, UT (US)

(73) Assignee: Optium, LLC, Provo, UT (US)

( * ) Notice: Subject to any disclaimer, the term of this patent is extended or adjusted under 35 U.S.C. 154(b) by 146 days.

(21) Appl. No.: 17/058,020

(22) PCT Filed: May 23, 2019

(86) PCT No.: PCT/US2019/033844
§ 371 (c)(1),
(2) Date: Nov. 23, 2020

(87) PCT Pub. No.: WO2019/226950
PCT Pub. Date: Nov. 28, 2019

(65) Prior Publication Data
US 2021/0196769 A1    Jul. 1, 2021

Related U.S. Application Data

(60) Provisional application No. 62/815,844, filed on Mar. 8, 2019, provisional application No. 62/675,652, filed on May 23, 2018.

(51) Int. Cl.
| | | |
|---|---|---|
| A61K 35/76 | (2015.01) | |
| A61K 35/745 | (2015.01) | |
| A61K 35/747 | (2015.01) | |
| A61K 35/00 | (2006.01) | |

(52) U.S. Cl.
CPC ............ *A61K 35/76* (2013.01); *A61K 35/745* (2013.01); *A61K 35/747* (2013.01); *A61K 2035/115* (2013.01)

(58) Field of Classification Search
None
See application file for complete search history.

(56) References Cited

U.S. PATENT DOCUMENTS

| | | |
|---|---|---|
| 2011/0123501 A1 | 5/2011 | Chou et al. |
| 2015/0297648 A1 | 10/2015 | Deaton et al. |
| 2016/0184370 A1 | 6/2016 | McKenzie et al. |

FOREIGN PATENT DOCUMENTS

| | | |
|---|---|---|
| EP | 2799063 A1 | 11/2014 |
| KR | 10-2016-0005728 A | 1/2016 |
| KR | 10-1670048 B1 | 10/2016 |
| WO | 03/00274 A2 | 1/2003 |
| WO | 2015/104388 A1 | 7/2015 |
| WO | 2016003307 A1 | 1/2016 |
| WO | 2019048930 A2 | 3/2019 |

OTHER PUBLICATIONS

Rhoads DD, Wolcott RD, Kuskowski MA, Wolcott BM, Ward LS, Sulakvelidze A. Bacteriophage therapy of venous leg ulcers in humans: results of a phase I safety trial. J Wound Care. Jun. 2009; 18(6):237-8, 240-3. doi: 10.12968/jowc.2009.18.6.42801. PMID: 19661847.*
GenBank accession NC_023561.1. Mar. 4, 2014.*
GenBank accession KX534339.1. Aug. 8, 2016.*
GenBank accession KY780482.1. May 6, 2017.*
GenBank accession MF285620.1. Sep. 17, 2017.*
Mishra CK, Choi TJ, Kang SC. Isolation and characterization of a bacteriophage F20 virulent to Enterobacter aerogenes. J Gen Virol. Oct. 2012;93(Pt 10):2310-2314. doi: 10.1099/vir.0.043562-0. Epub Jul. 4, 2012. PMID: 22764320.*
Parvataneni S, Mijalis EM, Kuty Everett GF, Rasche ES, Liu M, Gill JJ. Complete Genome Sequence of Citrobacter freundii Myophage Mijalis. Genome Announc. Aug. 3, 2017;5(31): e00228-17. doi: 10.1128/genomeA.00228-17. PMID: 28774966; PMCID: PMC5543628.*
GenBank accession LT614807. Sep. 15, 2016.*
Andrezal et al., Characterization and the host specificity of Pet-CM3-4, a new phage infecting Cronobacter and Enterobacter strains , 2023, Virus Research, vol. 324, pp. 1-9.*
Genbank Accession NC_049834, Jan. 10, 2023.*
International Search Report dated Jul. 23, 2018, issued in PCT Application No. PCT/US2018/022419, filed Mar. 14, 2018.
J. G. Zhao et al., Combating Obesity Through Gut Microbiome Targeted Bacteriophage Therapy, Library Undergraduate Poster Competition 2017, Mar. 18, 2017, p. 1.

(Continued)

*Primary Examiner* — Janet L Andres
*Assistant Examiner* — Jeffrey Mark Sifford
(74) *Attorney, Agent, or Firm* — Workman Nydegger

(57) ABSTRACT

Compositions for affecting the intestinal microbiome of a mammalian subject can include a pharmaceutically-acceptable carrier and greater than or equal to $1\times10^4$ PFU/mL or PFU/mg of bacteriophage having a tropism that includes an obesogenic and/or inflammatory bacterium associated with an intestinal microbiome of a mammal. Processes for preparing the disclosed compositions can include isolating the bacteriophage from an environmental source, characterizing the bacteriophage, and combining the bacteriophage with the pharmaceutically acceptable carrier at greater than or equal to $1\times10^4$ PFU/mL or PFU/mg. Methods can include administering the disclosed compositions to a mammalian subject with or without co-administration of the disclosed probiotics. Administering the disclosed compositions can reduce a concentration of obesogenic and/or inflammatory bacteria in the intestinal microbiome of the mammalian subject, promote or induce weight loss, reduce inflammation, support metabolic health, and/or support a healthy balance/diversity within the intestinal microbiome of the mammalian subject.

20 Claims, 8 Drawing Sheets
Specification includes a Sequence Listing.

(56) References Cited

OTHER PUBLICATIONS

Magdalena et al., "Human Microbiome: When a Friend Becomes an Enemy", Archivum Immunologiae ET Therapiae Experimentalis, vol. 63, No. 4, Feb. 15, 2015, pp. 287-298.
N. Fei et al., An Opportunistic Pathogen Isolated from the Gut of an Obese Human Cases Obesity in Germfree Mice, the ISME Journal, 2012, pp. 1-5.
Written Opinion dated Jul. 23, 2018, issued in PCT Application No. PCT/US2018/022419, filed Mar. 14, 2018.
Y. Xu et al., Bacteriophage Therapy Against Enterobacteriaceae, Virologica Sinica, Feb. 2015, vol. 30, No. 1, pp. 11-18.
Gogokhia et al. Expansion of Bacteriophages Is Linked to Aggravated Intestinal Inflammation and Colitis, Cell Host & Microbe 25, 285-299. e1-e8, Feb. 13, 2019.
Parmar et al. Genomic characterization of key bacteriophages to formulatethe potential biocontrol agent to combat enteric pathogenic bacteria, Archives of Microbiology, 2018, 200, p. 611-622.
European Search Report dated Mar. 21, 2022, issued in PCT Application No. PCT/US2019033844.

\* cited by examiner

| Host bacterium | Phage Name | Bacteria Tested Against ||||||||
|---|---|---|---|---|---|---|---|---|---|
| | | Enterobacter cloacae | Escherichia coli | Serratia marcescens | Klebsiella pneumoniae | Enterobacter aerogenes | Kluyvera ascorbata | Citrobacter freundii | Yokenella regensburgei |
| E. cloacae | Opt-126 | X | X | | | X | X | | X |
| | Opt-712 | X | | | | | | | |
| | Opt-125 | X | | | | | | | |
| | Opt-18 | X | | | | | | | |
| | Opt-38 | X | | | | | | | |
| E. coli | Opt-719 | | X | | X | X | | | |
| | Opt-212 | | X | | X | | | | |
| | Opt-819 | | X | | X | | | | |
| S. marcescens | Opt-162 | | | X | | | | | |
| | Opt-155 | | | X | | | | | |
| | Opt-169 | | | X | | | | | |
| | Opt-148 | | | X | | | | | |
| K. pneumoniae | Opt-817 | | X | | X | | | | |
| | Opt-79 | X | | | X | | | | |
| | Opt-12 | X | | | X | | | | |
| E. aerogenes | Opt-747 | | | | | X | | | |
| | Opt-82 | | | | | X | | | |
| | Opt-35 | | | | | X | | | |
| | Opt-688 | | | | | X | | | |
| | Opt-971 | | X | | | X | X | | |
| | Opt-27 | | | | | X | | | |
| K. ascorbata | Opt-121 | | | | | | X | X | X |
| | Opt-67 | | | | | | X | X | X |
| | Opt-531 | | | | | | X | X | X |
| | Opt-502 | | | | | | X | X | X |
| C. freundii | Opt-574 | | | | | | | X | |
| | Opt-219 | | | | | | | X | |
| | Opt-716 | | | | | | X | X | |
| | Opt-225 | | | | | | | X | |
| | Opt-117 | | | | | | | X | |
| | Opt-24 | | X | | | | | X | |
| Y. regensburgeii | Opt-304 | | | | | | X | | X |
| | Opt-835 | | | | | | X | | X |
| | Opt-812 | | | | | | X | | X |
| | Opt-46 | | | | | | X | | X |
| | Opt-116 | | | | | | X | | X |
| | Opt-356 | | | | | | | | X |

FIG. 3

BACTERIOPHAGE COMPOSITIONS AND KITS AND RELATED METHODS

CROSS-REFERENCE TO RELATED APPLICATIONS

This application is a nationalization of international application Ser. No. PCT/US2019/033844, filed May 23, 2019, which claims priority to and the benefit of U.S. Provisional Patent Application Ser. No. 62/675,652, filed May 23, 2018 and titled "METHODS AND COMPOSITIONS FOR TREATING CHRONIC DISEASES WITH BACTERIOPHAGES" and to U.S. Provisional Patent Application Ser. No. 62/815,844, filed Mar. 8, 2019 and titled "PHAGE COMPOSITIONS AND METHODS OF USE." Each of the foregoing are incorporated herein by this reference in their entirety.

TECHNICAL FIELD

The present disclosure generally relates to compositions that include one or more bacteriophages, kits including the same, and methods for preparing such compositions and for using or administering such compositions to impact the number or concentration of bacteria within the intestinal microbiome of a mammalian subject, preferably to promote or induce weight loss, reduce inflammation, support metabolic health, and/or support a healthy balance/diversity within the gut microbiome.

BACKGROUND

Obesity has become an epidemic worldwide. Overweight and obesity rates in the United States have increased dramatically over the past few decades, culminating in 37% of Americans (i.e., 120 million people) qualifying as obese. In the United States the prevalence of obesity was 35% among men and 40% among women in 2013 to 2014. Another 34% of American adults are overweight. Six percent of American adults are morbidly obese, which is a 400% increase since 1986. Among children and adolescents, the prevalence of obesity is 17%. Obesity is often accompanied by chronic low-level inflammation and is the major contributor to many other chronic illnesses such as type 2 diabetes, insulin resistance, pre-diabetes, heart disease, stroke, fatty liver disease, kidney disease, osteoarthritis, depression, anxiety, certain cancers, and/or other conditions that often result in diminished quality of life and skyrocketing healthcare costs.

In an effort to increase their quality of life, some overweight or obese individuals have adopted a restricted calorie diet and/or increased their physical activity, such as by participating in a cardiovascular fitness regimen. However, certain physical limitations can hamper an individual's efforts to lose weight. For example, some overweight or obese individuals have difficulty increasing the level or intensity of their physical activity due to complications or secondary effects of their size and weight. For some overweight or obese individuals, their weight loss progress is unexpectedly slow or at times non-existent—even with strict adherence to diet and exercise programs.

Recent evidence has suggested that other factors outside of diet and exercise may play a role in an individual's ability to promote or induce weight loss. For example, an individual may be genetically predisposed to having a higher body mass index and/or poor metabolism. Environmental pressures may compound genetic predispositions and play a role in an individual's ability to promote or induce weight loss. Recently it has been hypothesized that an individual's ability to absorb digested nutrients can impact their health and wellness and may influence the effectiveness of dieting or other weight loss programs.

More recently, scientists have been able to identify correlations between the metabolic potential of mammals and the diversity and makeup of their respective intestinal microbiome. For example, seminal studies in mice have correlated pregnancy-induced insulin resistance with the makeup and diversity of the mouse's intestinal microbiome. Fecal transplants between pregnant mice exhibiting pregnancy-induced insulin resistance and non-pregnant mice having normal or baseline insulin sensitivity caused the non-pregnant mice to exhibit signs and symptoms of pregnancy-induced insulin resistance—similar to their pregnant counterparts. In another study, fecal transplants from obese mice to healthy, average weight mice caused the average weight mice to gain weight even though the mice were maintained on the same diet.

These studies and others have implicated the intestinal microbiome as playing a role in our digestive and metabolic health. Unfortunately, it has proven difficult to tease apart the complex interplay between the state of an individual's intestinal microbiome and the respective effects that may have on their physiology and metabolism. The intestinal microbiome is a complex ecosystem of bacteria, fungi, and viruses existing in different physiological states and structures. Bacteria within the intestinal microbiome, for example, can exist as planktonic cells or as structured communities of monoclonal—or even polyclonal—biofilms. Additionally, some bacterial species may localize to distinct regions within the gut, and the practical implications of the spatial organization of gut-associated microbes is poorly understood. Further complicating matters, the makeup and diversity of gut-associated microbes varies between individuals, and few commonalities or predictive features of a "healthy" intestinal microbiome are known.

Most research in this area has relied on whole fecal transplants between hosts to identify global correlations between physiological states and the content and diversity of associated intestinal microbiomes. This is due, in part, to the expansive diversity and proportional concentration of microbes that make up the intestinal microbiome of mammals. Many of the intestinal microbiota are not culturable using known laboratory conditions and media, which further complicates their identification and tractable contribution to the host's physiology or metabolism. Thus, while the study of the intestinal microbiome has provided some provocative insights, there is a lack of tools to specifically augment the membership or concentration of a selective cohort of microbes within the mammalian microbiome. This is painfully evident with respect to the lack of tools and methods available for transforming the mammalian microbiome from an undesirable state to a desirable state.

For example, aspects of the microbiome have been shown to correlate with weight (e.g., body mass index, BMI) and obesity. Cohorts of bacteria associated with the intestinal microbiome have been correlated with "healthy" individuals having an average or ideal BMI, while other bacteria associated with the intestinal microbiome have been correlated with "unhealthy" overweight or obese individuals. However, there is a dearth of compositions, methods, and/or kits for reducing or eliminating microbes associated with obesity and/or for increasing the prevalence of "beneficial" microbes associated with non-obese individuals.

Accordingly, there are a number of disadvantages associated with currently available compositions, methods, and kits that can be addressed, and there is a need for targeted approaches of meaningfully affecting changes to the microbiome to improve the health and well-being of individuals, particularly with respect to weight gain, obesity, and the deleterious consequences associated therewith.

SUMMARY

Embodiments of the present disclosure solve one or more of the foregoing or other problems in the art with compositions, methods, and kits for affecting changes to the intestinal microbiome. In particular, aspects (or embodiments) of the present disclosure relate to methods, systems, and compositions for reducing the amount or concentration of one or more bacterium and, in certain aspects, increasing the amount or concentration of one or more additional bacterium, in the intestinal microbiome of a mammalian, preferably human, subject. Specifically, aspects of the present disclosure relate to methods, systems, and compositions for treating one or more conditions resulting, at least in part, from the overpopulation of the one or more bacterium and/or the underpopulation of the one or more additional bacterium in the gut of said subject. Such conditions can include, for example, (i) obesity (or over-weight), (ii) one or more obesity-(or over-weight-) associated condition (e.g., (metabolic, chronic, and/or acute) illnesses, disorders, and/or diseases), (iii) inflammation, particularly low-level, systemic inflammation, and/or (iv) one or more inflammation-associated conditions (e.g., (metabolic, chronic, and/or acute) illnesses, disorders, and/or diseases). Embodiments include one or more bacteriophage, and compositions or kits comprising the same, and processes for preparing and using said compositions or kits.

Aspects of the present disclosure include a composition comprising an amount of one or more bacteriophage and a pharmaceutically acceptable carrier or excipient.

The composition, or bacteriophage thereof, of various aspects of the present disclosure can be useful and/or effective for altering or to alter the intestinal microbiome or the composition of the intestinal microbiome of a mammalian subject when the composition is administered to the subject in a manner that delivers or disposes the composition, or the one or more bacteriophage thereof, into the gut or intestinal microbiome of the subject. For example, the composition, or bacteriophage thereof, can be useful and/or effective for reducing the concentration of one or more bacterium in the intestinal microbiome of the subject, when administered to the subject in a manner that delivers or disposes the composition, or the one or more bacteriophage thereof, into the gut or intestinal microbiome of the subject. In certain aspects, the one or more bacterium can include at least one species or strain of obesogenic, inflammatory, and/or other bacteria. The one or more bacteriophage can have tropism for (or that includes) the one or more (obesogenic, inflammatory, and/or other) bacterium, or species or strain thereof.

In at least one aspect, reducing the concentration of the one or more obesogenic, inflammatory, and/or other bacteria in the intestinal microbiome of the subject can be effective to: induce, promote, and/or support weight loss; treat obesity (or over-weight) and/or one or more obesity-associated condition; promote or support weight management; support metabolic health; support a healthy balance and/or diversity within the gut microbiome, treat and/or reduce (low-level, systemic) inflammation, reduce the presence and/or concentration of inflammatory markers; and/or treat one or more condition associated with (low-level systemic) inflammation, in the subject. In some aspects, a condition associated with obesity and/or associated with (low-level systemic) inflammation can include one or more of type 2 diabetes, insulin resistance, pre-diabetes, heart disease, stroke, fatty liver disease, kidney disease, osteoarthritis, depression, anxiety, certain cancers, and/or other disorder, illness, disease, and/or condition, including metabolic and/or acute disorders, illnesses, and/or diseases. Accordingly, aspects of the present disclosure relate to compositions for use in treating (i) obesity and/or one or more obesity-associated condition in the subject, (ii) inflammation and/or one or more condition associated with (low-level systemic) inflammation in the subject, (iii) over-population of one or more bacterium in the intestinal microbiome of the subject, and (iv) combinations thereof.

In at least one aspect, reducing the concentration of the one or more obesogenic, inflammatory, and/or other bacteria in the intestinal microbiome of the subject can be effective to: increase energy and/or improve stamina, improve regularity and ease of bowel movements (with softer stools and/or reduced/less-frequent constipation), reduce appetite/food cravings, improve muscle tone, reduce inches around arms and/or waist, improve complexion and/or reduced acne, improve mood, reduce feeling of depression, improve concentration, mental awareness and/or focus, reduce and/or alleviate chronic stomach pain, and/or improve overall well-being. Accordingly, compositions of the present disclosure can be used to treat a variety of conditions, ranging from obesity (or over-weight), stomach pain, constipation, and food cravings, to low-energy or stamina, impaired mental focus, depression/mood disorders, and ache/skin conditions.

One or more aspects (or embodiments) of the present disclosure include a composition having a pharmaceutically-acceptable carrier and one or more bacteriophage, the one or more bacteriophage being included in the composition in any suitable amount and/or concentration. For example, one or more bacteriophage can be included in the composition in an amount and/or concentration effective to reduce the concentration of one or more (target or host) bacterium of the one or more bacteriophage when the composition is administered to a mammalian, preferably human, subject in a manner that delivers or disposes the composition, or one or more bacteriophage thereof, into the gut or intestinal microbiome of the subject. Illustratively, the composition can have or comprise (i) greater than or equal to $1 \times 10^4$ of the one or more bacteriophage, (ii) greater than or equal to $1 \times 10^4$ plaque forming units of the one or more bacteriophage, (iii) greater than or equal to $1 \times 10^4$ PFU per milliliter (PFU/mL) of the one or more bacteriophage, and/or (iv) greater than or equal to $1 \times 10^4$ PFU per milligram (PFU/mg) of the one or more bacteriophage. As used herein, the "effective" amount can be or comprise any of the foregoing or other specific amounts or concentrations.

In certain aspects, the one or more bacteriophage (of the composition) has a tropism for or that includes the one or more species or strain of bacterium. Illustratively, the one or more bacteriophage can have a tropism for or that includes a single species or strain of bacterium, or a plurality of (e.g., closely-related) bacterium. In other aspects, the one or more bacteriophage can have a tropism for or that includes a plurality of bacterium that are not closely related.

In some aspects, the composition includes one, or a single (strain of) bacteriophage. The single (strain of) bacteriophage can a tropism for or that includes a single species or strain of bacterium, or a plurality of bacterium. In other aspects, the composition includes a plurality of (strains of) bacteriophage. In at least one aspect, the plurality of (strains of) bacteriophage can include a first (strain of) bacteriophage, a second (strain of) bacteriophage, an optional third, fourth, fifth, sixth, and so forth, (strains of) bacteriophage. The plurality of (strain of) bacteriophage can each have a tropism for or that includes a single (species or strain of) bacterium, or a plurality of (species or strains of) bacteria. The single (species or strain of) bacterium can be the same bacterium or different bacterium. The plurality of (species or strains of) bacteria can be the same plurality of bacteria or different bacteria. Illustratively, the first (strain of) bacteriophage can have a tropism for or that includes a single (species or strain of) bacterium, or a plurality of (species or strains of) bacteria, and the second (strain of) bacteriophage can have a tropism for or that includes the same or a different single (species or strain of) bacterium, or the same or a different plurality of (species or strains of) bacteria.

In at least one aspect, a mixture (or cocktail) of bacteriophages can be selected to include in a composition of the present disclosure. The cocktail of bacteriophages can be configured for, adapted for, or otherwise capable of targeting, infecting, and killing (e.g. lysing) includes a single (species or strain of) bacterium, or a plurality of (species or strains of) bacteria. Redundancy or overlap in tropism may be desirable in some aspects of the present disclosure. Variety and diversity in tropism may be desirable in some aspects of the present disclosure. For example, some subjects may have an imparlance in a single species or strain of bacterium in their gut microbiome, while other may have an imparlance in a plurality of species or strains of bacteria in their gut microbiome. Different combinations or two or more bacteriophage can be selected to target the single or plurality of bacteria. Moreover, the bacteria may be adapted to or capable of mutating to escape targeting, infection, or destruction by one or more strains of bacteriophage. Accordingly, compositions according to some aspects of the present disclosure include at least two bacteriophage have tropism for the same bacterium or at least some of the same bacteria, but preferably through different (genetic or tropic) mechanisms of action.

In at least one aspect, the composition comprises a pharmaceutically-acceptable carrier and an amount of one or more bacteriophage. The amount of the one or more bacteriophage can be (i) an amount effective to reduce the concentration of one or more target bacterium of the one or more bacteriophage when the composition is administered to a mammalian, preferably human, subject in a manner that delivers or disposes the composition, or one or more bacteriophage thereof, into the gut or intestinal microbiome of the subject, (ii) greater than or equal to $1\times10^4$ of the one or more bacteriophage, (iii) greater than or equal to $1\times10^4$ plaque forming units of the one or more bacteriophage, (iv) greater than or equal to $1\times10^4$ PFU per milliliter (PFU/mL) of the one or more bacteriophage, (v) and/or greater than or equal to $1\times10^4$ PFU per milligram (PFU/mg) of the one or more bacteriophage. The one or more bacteriophage can have a tropism that comprises, or exhibits a specific infectivity to, one or more target bacterium associated with the intestinal microbiome of the subject. The one or more target bacterium can be or comprise one or more obesogenic and/or inflammatory bacterium associated with an intestinal microbiome of a mammal.

In at least one aspect, the composition comprises a pharmaceutically-acceptable carrier and an amount of two or more bacteriophage. The amount of each of the two or more bacteriophage can be (i) an amount effective to reduce the concentration of one or more target bacterium of each of the two or more bacteriophage when the composition is administered to a mammalian, preferably human, subject in a manner that delivers or disposes the composition, or two or more bacteriophage thereof, into the gut or intestinal microbiome of the subject, (ii) greater than or equal to $1\times10^4$ of each of the two or more bacteriophage, (iii) greater than or equal to $1\times10^4$ plaque forming units of each of the two or more bacteriophage, (iv) greater than or equal to $1\times10^4$ PFU per milliliter (PFU/mL) of each of the two or more bacteriophage, (v) and/or greater than or equal to $1\times10^4$ PFU per milligram (PFU/mg) of each of the two or more bacteriophage. Each of the two or more bacteriophage can have a tropism that comprises, or exhibit a specific infectivity to, one or more target bacterium associated with the intestinal microbiome of the subject. The one or more target bacterium can be or comprise one or more obesogenic and/or inflammatory bacterium associated with an intestinal microbiome of a mammal. The tropism of each of the two or more bacteriophage can be a similar or same tropism, or a different tropism, than any one or more other bacteriophage of the composition.

In one aspect, the composition comprises a pharmaceutically-acceptable carrier and greater than or equal to $1\times10^6$ or $1\times10^6$ PFU, etc. of (each of) a plurality of bacteriophages, the plurality of bacteriophages comprising two or more of, preferably each of, Optium-12, Optium-18, Optium-38, Optium-79, Optium-125, Optium-126, Optium-148, Optium-155, Optium-162, Optium-169, Optium-212, Optium-712, Optium-719, Optium-712, and Optium-819, corresponding to corresponding to SEQ ID NOs 1-15 of the present disclosure. In one aspect, the composition comprises a pharmaceutically-acceptable carrier and greater than or equal to $1\times10^8$ or $1\times10^8$ PFU, etc. of each of a plurality of bacteriophages, the plurality of bacteriophages comprising, consisting of, or consisting essentially of Optium-12, Optium-18, Optium-38, Optium-79, Optium-125, Optium-126, Optium-148, Optium-155, Optium-162, Optium-169, Optium-212, Optium-712, Optium-719, Optium-712, and Optium-819, corresponding to corresponding to SEQ ID NOs 1-15 of the present disclosure.

One or more embodiments of the present disclosure include a composition having a pharmaceutically-acceptable carrier and greater than or equal to $1\times10^4$ plaque forming units per milliliter (PFU/mL), per milligram (PFU/mg), or other suitable unit of measurement, of one or more bacteriophage that has a tropism that includes one or more obesogenic bacterium associated with an intestinal microbiome of a mammal. In at least one aspect of the composition, the tropism of the one or more bacteriophage comprises *Enterobacter cloacae*, preferably *Enterobacter cloacae* strain B29. In at least one aspect of the composition, the one or more bacteriophage comprises Optium-18, Optium-38, Optium-125, Optium-126, and/or Optium-712.

In at least one aspect of the composition, the one or more bacteriophage comprises Optium-12, Optium-18, Optium-38, Optium-79, Optium-125, Optium-126, Optium-148, Optium-155, Optium-162, Optium-169, Optium-212, Optium-712, Optium-719, Optium-712 and/or Optium-819.

In one additional aspect the one or more bacteriophage comprises Optium-17, Optium-34, Optium-86, Optium-88, Optium-113, Optium-118, Optium-125, and/or Optium-417.

In at least one aspect, the one or more bacteriophage of the composition has a tropism that comprises one or more of *Escherichia coli, Serratia marcescens, Klebsiella pneumoniae, Enterobacter aerogenes* (also classified as *Klebsiella aerogenes*), *Citrobacter freundii, Kluyvera ascorbata*, and *Yokenella regensburgei*.

In at least one aspect, the one or more bacteriophage are classified or typed as, or have a classification selected from the group consisting of: Myoviridae, preferably (i) T4-like, more preferably sub cluster G, I, or a new or unknown subcluster type, or (ii) RV5-like, more preferably subcluster C or a new or unknown subcluster type; Podoviridae, preferably T7-like, more preferably subcluster B or a new or unknown subcluster type; Siphoviridae, preferably (i) S01-like, more preferably subcluster A or a new or unknown subcluster type, (ii) 9g-like, more preferably subcluster B or a new or unknown subcluster type, (iii) T1-like, more preferably subcluster B, D, or a new or unknown subcluster type; Jello cluster, preferably subcluster A, B, or a new or unknown subcluster type; FaintSaint cluster; and Phage T1-like.

In at least one aspect, the one or more bacteriophage is lytic.

In at least one aspect, the pharmaceutically-acceptable carrier and the one or more bacteriophage form an aqueous solution further comprising salt, peptides, and/or yeast extract.

In at least one aspect, the aqueous solution comprises greater than or equal to 0.5 mg/mL salts, greater than 0.5 mg/mL peptides, and greater than 0.25 mg/mL yeast extract.

In at least one aspect, the one or more bacteriophage is present (in the composition) at a concentration greater than or equal to $1\times10^5$, $1\times10^6$, $1\times10^7$, $1\times10^8$, $1\times10^9$, or $1\times10^{10}$ PFU/mL or PFU/mg.

In at least one aspect, the composition further comprises greater than or equal to $1\times10^4$ (or $1\times10^5$, etc.) PFU/mL or PFU/mg of one or more additional bacteriophage having a respective tropism that comprises one or more additional bacterium associated with the intestinal microbiome of a mammal. In at least one aspect, the one or more additional bacterium comprises one or more of: *Enterobacter cloacae*, *Escherichia coli*, *Serratia marcescens*, *Klebsiella pneumoniae*, *Enterobacter aerogenes*, *Kluyvera ascorbata*, *Citrobacter freundii*, or *Yokenella regensburgei*. In at least one aspect of the composition, the one or more additional bacterium comprises one or more of *Clostridium ramosum* or *Bilophila wadsworthia*.

In at least one aspect, the one or more bacteriophage comprises one or more of: a first bacteriophage having a tropism that comprises at least *Enterobacter cloacae*, a second bacteriophage having a tropism that comprises at least *Klebsiella pneumoniae*, a third bacteriophage having a tropism that comprises at least *Escherichia coli*, or a fourth bacteriophage having a tropism that comprises at least *Serratia marcescens*. In at least one aspect of the foregoing composition, the first bacteriophage can include one or more of Optium-18, Optium-38, Optium-125, Optium-126, and/or Optium-712; the second bacteriophage can include one or more of Optium-12, Optium-79, and/or Optium-817; wherein the third bacteriophage can include one or more of Optium-212, Optium-719, and/or Optium-819; and/or the fourth bacteriophage can include one or more of Optium-148, Optium-155, Optium-162, and/or Optium-169.

In at least one aspect, the one or more bacteriophage comprises one or more of a fifth bacteriophage having a tropism that comprises at least *Enterobacter aerogenes* (also classified as *Klebsiella aerogenes*), a sixth bacteriophage having a tropism that comprises at least *Kluyvera ascorbata*, a seventh bacteriophage having a tropism that comprises at least *Citrobacter freundii*, and/or an eighth bacteriophage having a tropism that comprises at least *Yokenella regensburgei*.

Methods of the present disclosure can also include a process for preparing the disclosed compositions. Aspects of the disclosed methods for preparing the compositions can include aspects of the compositions disclosed herein. In at least one aspect, a method for preparing the disclosed compositions includes isolating the one or more bacteriophage from an environmental source, characterizing the one or more bacteriophage, and combining the one or more bacteriophage with the pharmaceutically acceptable carrier at greater than or equal to $1\times10^4$ (or $1\times10^5$, etc.) PFU/mL or PFU/mg.

In at least one aspect, the one or more bacteriophage has a genome with greater than or equal to 80% sequence identity to one of SEQ ID NOs 1-19, preferably one or SEQ ID NOs 1-15. In at least one aspect, the one or more bacteriophage has a genome with greater than or equal to 85%, 88%, 90%, 92%, 94%, 95%, 96%, 97%, 98%, or 99% sequence identity to one of SEQ ID NOs 1-19, preferably one or SEQ ID NOs 1-15. Alternatively, the one or more bacteriophage can have a genome with a tropic element having greater than or equal to 80%, 85%, 88%, 90%, 92%, 94%, 95%, 96%, 97%, 98%, or 99% sequence identity to a tropic element of one of SEQ ID NOs 1-19, preferably one or SEQ ID NOs 1-15.

In at least one aspect of the method, characterizing the one or more bacteriophage can include measuring a lytic activity of the one or more bacteriophage to determine that the one or more bacteriophage is not lysogenic and determining a tropism for the one or more bacteriophage. In at least one aspect the tropism comprises a narrow host range that includes the one or more obesogenic, inflammatory, and/or other bacterium.

In at least one aspect of the method, characterizing the one or more bacteriophage can additionally or alternatively include sequencing the genome of the one or more bacteriophage and excluding from the composition any bacteriophage having a genome that comprises a toxin or virulence factor gene or an integrase gene. One aspect of the foregoing methods can include determining, based on the sequenced genome, a relatedness of the one or more bacteriophage to a second bacteriophage having a related tropism.

In at least one aspect of the method, combining the one or more bacteriophage with the pharmaceutically acceptable carrier includes combining a plurality of bacteriophages with the pharmaceutically acceptable carrier where the plurality of bacteriophages comprises at least a first set of bacteriophages sharing a tropism that includes the one or more obesogenic, inflammatory, and/or other bacterium. In at least one aspect of the foregoing method, the first set of bacteriophages comprises two bacteriophages having a different host cell receptor specificity for attachment and/or that have less than or equal to 97% genomic sequence identity, preferably less than or equal to 90% genomic sequence identity, or more preferably less than or equal to 80% genomic sequence identity.

Kits of the present disclosure can include a composition and a probiotic and/or prebiotic. In at least one aspect of the kit, the composition includes a pharmaceutically-acceptable carrier and greater than or equal to $1\times10^4$ (or $1\times10^5$, etc.) PFU/mL or PFU/mg of one or more bacteriophage having a tropism that comprises one or more obesogenic, inflammatory, and/or other bacterium associated with an intestinal microbiome of a mammal.

In at least one aspect of the kit, the probiotic comprises a mixture of bacteria comprising *Bifidobacterium* sp. and *Lactobacillus* sp.

In at least one aspect of the kit, the probiotic comprises one or more of: *Lactobacillus rhamnosus, Lactobacillus reuteri, Bacteroides fragilis, Bifidobacterium breve, Bifidobacterium longum, Bifidobacterium pseudocatenulatum*. In at least one aspect, the probiotic of the kit can additionally or alternatively include one or more of: *Lactobacillus acidophilus, Lactobacillus brevis, Lactobacillus casei, Lactobacillus salivarius, Lactobacillus lactis, Bifidobacterium bifidum*, or *Bifidobacterium lactis*. In at least one aspect, the probiotic of the kit can additionally or alternatively include one or more of: *Bifidobacterium infantis, Lactobacillus plantarum, Lactobacillus delbrueckii, Lactobacillus bulgaricus, Lactococcus cremoris*, or *Enterococcus faecium*. In at least one aspect, the probiotic of the kit can additionally or alternatively include one or more of *Roseburia hominis, Akkermansia mucimphila*, or *Faecalibacterium prausnitzii*. In at least one aspect, the probiotic of the kit can additionally or alternatively include one or more bacterium of the Lachnospiraceae family.

In at least one aspect, a kit can include any of the compositions disclosed herein and any of the probiotics disclosed herein.

Methods of the present disclosure can also include administering a composition to a mammalian subject, preferably in a manner that delivers or disposes the composition, or the one or more bacteriophage thereof, into the gut or intestinal microbiome of the subject. In at least one aspect of the method, the composition includes a pharmaceutically-acceptable carrier and greater than or equal to $1 \times 10^4$ (or $1 \times 10^5$, etc.) plaque forming units per milliliter (PFU/mL) or PFU per milligram (PFU/mg), of one or more bacteriophage, preferably having a tropism that comprises one or more obesogenic, inflammatory, and/or other bacterium associated with an intestinal microbiome of a mammal. In at least one aspect, the foregoing method can additionally include administering a probiotic to the mammalian subject, preferably in a manner that delivers or disposes the probiotic into the gut or intestinal microbiome of the subject. In at least one aspect, the administered probiotic comprises a mixture of bacteria comprising *Bifidobacterium* sp. and *Lactobacillus* sp. In at least one aspect, the administered probiotic comprises one or more of: *Lactobacillus rhamnosus, Lactobacillus reuteri, Bacteroides fragilis, Bifidobacterium breve, Bifidobacterium longum, Bifidobacterium pseudocatenulatum*. In at least one aspect, the administered probiotic can additionally or alternatively include one or more of: *Lactobacillus acidophilus, Lactobacillus brevis, Lactobacillus casei, Lactobacillus salivarius, Lactobacillus lactis, Bifidobacterium bifidum*, or *Bifidobacterium lactis*. In at least one aspect, the administered probiotic can additionally or alternatively include one or more of: *Bifidobacterium infantis, Lactobacillus plantarum, Lactobacillus delbrueckii, Lactobacillus bulgaricus, Lactococcus cremoris*, or *Enterococcus faecium*.

In at least one aspect of the disclosed methods, administering the composition to the mammalian subject reduces a concentration of one or more obesogenic bacterium in the intestinal microbiome of the mammalian subject. In at least one aspect, administering the composition to the mammalian subject additionally or alternatively promotes or induces weight loss in the mammalian subject. In at least one aspect, administering the composition to the mammalian subject reduces inflammation, supports metabolic health, and/or supports a healthy balance/diversity within the gut microbiome of the mammalian subject.

In at least one aspect of the disclosed methods, the composition is co-administered with any one of the disclosed probiotics.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which:

FIG. 2A illustrates a graphical representation depicting hsCRP results of a cohort of participants whose hsCRP levels were above the healthy range at the start of the study. FIG. 2B illustrates a graphical representation of the hsCRP results for all participants. FIG. 2C illustrates a graphical representation of participants' reduction in body weight. FIG. 2D illustrates a graphical representation of the participants' reduction in body mass index (BMI). FIG. 2E illustrates a graphical representation of the participants' increase in high-density lipoprotein (HDL) cholesterol. FIG. 2F illustrates a graphical representation of the participants' fasting blood glucose levels. FIGS. 2G and 2H illustrate graphical representations of participants' alanine aminotransferase (ALT) and aspartate aminotransferase (AST) levels, respectively. FIG. 2I illustrates a graphical representation of the participants' triglyceride levels.

FIG. 3 illustrates a table illustrating the tropism of select bacteriophages of the present disclosure.

DETAILED DESCRIPTION

Figure 1:
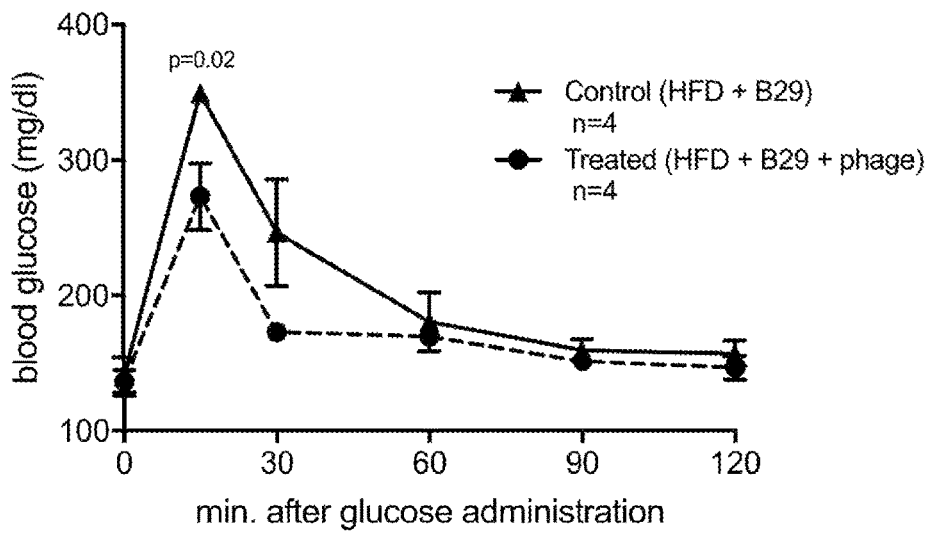
FIG. 1 is a graphical representation showing improved glucose tolerance in mice with intestinal microbiotas colonized with *Enterobacter cloacae* strain B29 treated for 8 weeks with bacteriophages as compared to control mice with intestinal microbiotas colonized with *Enterobacter cloacae* strain B29 but not treated with bacteriophages. All mice were on a high fat diet throughout the experiment.

Before describing various embodiments of the present disclosure in detail, it is to be understood that unless otherwise indicated, numbers expressing quantities, constituents, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

It should also be appreciated that any headings and subheadings used herein are for organizational purposes only and are not meant to be used to limit the scope of the description or the claims.

PCT Application No. PCT/US18/22419 filed Mar. 14, 2018, is incorporated by reference herein in its entirety.

Overview of Disclosed Embodiments

It has only recently become appreciated that dysbiosis of the gut microbiota fosters obesity. There is an on-going effort to identify causative bacterial strains within the microbiota of obese individuals. Evidence suggests that these "obesogenic bacteria" are not only associated with obesity but may also be associated with increased low-level inflammation throughout the body, which may impair insulin responsiveness and/or contribute to a variety of inflammation-associated conditions. Indeed, the obesogenic action of certain bacteria may originate, at least in part, in the inflammation-inducing activity of these bacteria. Obesogenic bacteria may also increase the host's ability to harvest and store energy from food.

The gram-negative opportunistic pathogen *Enterobacter cloacae* strain B29, isolated from the gut of an obese human, is the first human gut bacterium shown to cause obesity when transplanted into germ-free mice. Research using Koch's postulates showed that *Enterobacter cloacae* strain B29 causes obesity and chronic inflammation in its host. Another potentially obesogenic bacterium, *Clostridium ramosum*, is elevated in the gut microbiota of obese humans and also has an increased prevalence within the gut microbiota of women with type-2 diabetes. When transplanted into germ-free mice, *C. ramosum* has been shown to induce obesity.

It has been postulated that altering the composition or concentration of certain bacteria in the gut microbiome can support weight management, weight loss and/or contribute to the prevention and/or treatment of metabolic disorders. U.S. Publication 2011/0123501, for example, proposes strategies for modulating, in particular reducing, the amount of proteobacteria in the gut with compositions comprising an agent that reduces the amount of proteobacteria in the gut. The '501 publication focuses primarily on antibiotics for reducing the proteobacterial population in the gut and food grade bacteria, in particular probiotics, for further affecting the gut microbiome. In addition to the probiotic, the '501 publication also broadly lists prebiotics, yeasts, phytochemicals, and bacterial phages as potential components in the composition.

The '501 publication does not, however, disclose any actual bacteriophage or even which species of the nearly 50 enterobacteria genera listed in the specification are or should be targeted by said bacteriophages to reduce their prevalence in the gut and thereby afford some beneficial effect to its host. Indeed, there is no evidence in the publication that the group ever possessed, tested, classified, confirmed, formulated, and/or administered a single phage. Rather, the disclosure, with respect to phage-based compositions, is akin to a wish-list, acknowledging that there is a continued need in the art for a composition that comprises phage that can target and kill obesogenic bacteria in the gut.

Moreover, while the addition or introduction of a particular obesogenic bacterium to a host microbiome may cause or contribute to obesity, the inverse is not necessarily true. It is entirely unclear from the '501 publication whether simply reducing the concentration of the obesogenic bacterium within the host microbiome is sufficient to induce weight loss, particularly weight loss commensurate with the weight gain attributable to the introduction or presence of the obesogenic bacterium in the host's gut microbiome. While weight gain has been correlated with the introduction of *Enterobacter cloacae* strain B29, for example, into the mammalian gut microbiome, to the knowledge of the inventors, there is no objective data showing that the targeted removal of *Enterobacter cloacae* strain B29 or any other single obesogenic bacterium from the host microbiome causes or induces weight loss and/or promotes lasting weight loss.

Research has also shown rapid weight regain after diet-induced weight loss, due to persistence of what is assumed to be obesogenic bacteria within the hosts' gut microbiota. Accordingly, there is reason to believe that the composition of the gut microbiota is resistant to change, and while dieting can lead to temporary weight loss, it is likely occurring without restoring the gut microbiota to a balanced, "healthy" composition or diversity. As such, the presence or increased concentration of obesogenic bacteria within the host gut microbiome may cause an alteration in the membership or concentration of other microbes and thereby create an altered microbiota or altered gut environment that is conducive to weight gain or other undesirable effects.

The adverse or negative effects of so-called "bad" bacteria in the gut microbiome is often contributed to their production of endotoxins. Without being to any particular theory, gram negative bacteria are generally known to have or produce such endotoxins (e.g., as part of their cell wall). Bad bacteria in the gut microbiome may be gram negative, endotoxin-producing bacteria. Many so-called "good" bacteria in the gut microbiome are also gram negative. In a healthy gut, the endotoxin-laden good bacteria are not generally harmful; they are mostly commensal in nature. However, in situations of a so-called "leaky gut" (increased intestinal permeability, where bacteria and toxins are able to "leak" through the intestinal wall) or other similar pathologies, even good bacteria (or, more specifically, the endotoxins of or produced by said good bacteria) can cause (additional) inflammation or otherwise exacerbate certain condition.

To address these and other problems in the art, the compositions, kits, and methods of the present disclosure target and reduce the amount or concentration of obesogenic, inflammatory, and/or other bacteria within the intestinal microbiome. By reducing or eliminating these bacteria, ecological space is created for beneficial (or at least non-obesogenic) bacteria to thrive, which can improve the balance of the gut microbiota. The inventors of the present disclosure found that individuals experienced weight loss following administration of bacteriophage cocktails targeted to obesogenic bacteria. By targeting obesogenic bacteria using the disclosed compositions, individuals receive other unexpected physiological benefits beyond weight loss, such as reduced inflammation, supported metabolic health (e.g., increased high-density lipoprotein (HDL), decreased triglyceride levels, decreased fasting blood glucose levels, decreased alanine aminotransferase (ALT) levels, and decreased aspartate aminotransferase (AST) levels), and/or support of a healthy balance/diversity within the gut microbiome. Accordingly, compositions of the present disclosure can be useful and/or effective to reduce inflammation, support metabolic health (e.g., increased high-density lipoprotein (HDL), decrease triglyceride levels, decrease fasting blood glucose levels, decrease alanine aminotransferase (ALT) levels, decrease aspartate aminotransferase (AST) levels), and/or support a healthy balance/diversity within the gut microbiome.

Compositions of the present disclosure can provide a targeted therapy for conditions caused by or resulting, at least in part from, particular bacteria found in the mammalian gut microbiome. For example, compositions disclosed herein include one or more bacteriophages that specifically target and kill obesogenic, inflammatory, and/or other bacterium while not infecting human cells or killing non-target bacteria. Unlike broad-spectrum antibiotics, which indiscriminately kill, each of the one or more bacteriophages within the disclosed compositions has a narrow tropism, killing only a specific subset of bacterial genera and/or species. This beneficially allows the reduction and/or eradication of a targeted subset of bacteria—the obesogenic bacteria—while leaving unharmed other non-obesogenic bacteria within the microbiome.

Treatment with the inventive phage composition has been shown to lead to weight loss, improved glucose tolerance, and a reduction in inflammatory markers in human and/or mouse subjects. While not intending to be bound to any theory, bacteriophages can be (highly) specific to their target (or tropic) bacterial hosts. Accordingly, the down-stream effects of phage treatment (likely) result, directly and/or indirectly, from the reduction in target bacteria in the (gut microbiome) of the subject.

Treatment with the inventive phage composition to human subjects has also been shown to have the following beneficial effects: (i) increased energy and/or better stamina; (ii) greater regularity and ease of bowel movements with softer stools and/or reduced/less constipation; (iii) reduced appetite/food cravings; (iv) improved muscle tone and/or reduced inches around arms and/or waist; (v) improved complexion/skin and/or reduced acne; (vi) improved mood and/or better mental awareness; (vii) improved concentration and/or mental focus; (viii) reduced feeling of depression; (ix) reduced, alleviated, and/or elimination of chronic stomach aches; and/or (x) an overall positive impact. Accordingly, compositions of the present disclosure can be used to treat a variety of conditions, ranging from obesity (or over-weight), stomach pain, constipation, and food cravings, to low-energy or stamina, impaired mental focus, depression/mood disorders, and ache/skin conditions. The foregoing outcomes are also attributed to the reduction in target bacteria in the (gut microbiome) of the subject.

Various kits are additionally disclosed that include (i) a composition of the present disclosure, having one or more bacteriophage for reducing or eliminating one or more obesogenic, inflammatory, and/or other bacterium and (ii) a probiotic and/or prebiotic. Traditionally, probiotic foods and pills have proven unlikely and/or ineffective to produce lasting changes because bacterial species that are already stably established in the ecosystem of the gut microbiome have a strong advantage over newly introduced species. By combining the disclosed bacteria-killing composition with a probiotic, the kits disclosed herein provide an improved way of incorporating beneficial, probiotic bacteria into the gut microbiome while also beneficially preventing or resisting the targeted bacteria from returning to previously held positions and/or concentrations within the intestinal microbiome.

Compositions and Kits for Affecting the Intestinal Microbiome of a Mammal

Embodiments of the present disclosure include compositions that, when administered to a mammalian subject in a manner that delivers or disposes the composition, or the one or more bacteriophage thereof, into the gut or intestinal microbiome of the subject, affect the number or concentration of microbes constituting the subject's intestinal microbiome. In some exemplary embodiments, the subject is a mammal, preferably a human. A mammal includes any mammal, such as by way of non-limiting example, cattle, pigs, sheep, goats, horses, camels, buffalo, cats, dogs, rats, mice, and humans.

Each of the disclosed compositions includes a pharmaceutically-acceptable carrier in addition to one or more bacteriophages having a (narrow) tropism for one or more obesogenic, inflammatory, and/or other bacterium. As used herein, the term "tropism" is understood as the host range, number, and/or type of prokaryotes, preferably bacteria, that a given bacteriophage may successfully infect. A successful infection comprises the ability of a phage to bind and enter a host cell, replicate its genome and package the replicated genomes into capsids to form virion particles, and exit the host cell, preferably via a lytic event.

Some bacteriophages are understood to have broad microbial tropism, being capable of successfully infecting bacteria from different phylogenetic orders and/or greater than 10, preferably greater than 8, or more preferably greater than 6 different genera and/or species of bacteria within the same phylogenetic order, while other bacteriophages have a narrower tropism, being capable of successfully infecting, preferably, bacteria from the same phylogenetic order, more preferably only select genera and/or species of bacteria. In some instances, a bacteriophage may have a narrow tropism for bacteria derived from a single genera or bacterial species or strain. A bacteriophage having a "narrow tropism" is understood to be capable of successfully infecting less than or equal to 6, preferably less than or equal to 5, or more preferably less than or equal to 4, still more preferably less than or equal to 3, still more preferably less than or equal to 2, most preferably a single bacterial genera and/or species or strain, particularly within the *Enterobacter, Escherichia, Serratia, Klebsiella, Citrobacter, Kluyvera*, and *Yokenella* genera. In some embodiments, the tropism of the bacteriophage is limited to genera within the Enterobacteriaceae family.

In some embodiments, the composition includes a single bacteriophage having a narrow tropism. Such compositions can be useful to target and reduce the concentration of a single, or narrow range of, bacterial genera and/or species or strain in the mammalian gut. In at least one aspect, the bacteriophage is tropic for at least one *Enterobacter* sp., preferably *Enterobacter cloacae*, more preferably *Enterobacter cloacae* strain B29. The bacteriophage can include, for example, any one of Optium-18, Optium-38, Optium-125, Optium-126, and/or Optium-712.

In another aspect, the bacteriophage is tropic for at least one *Klebsiella* sp., preferably *Klebsiella pneumoniae*. The bacteriophage can include, for example, any one of Optium-12, Optium-79, and/or Optium-817.

In another aspect, the bacteriophage is tropic for at least one *Serratia* sp., preferably *Serratia marcescens*. The bacteriophage can include, for example, any one of Optium-148, Optium-155, Optium-162, and/or Optium-169.

In another aspect, the bacteriophage is tropic for at least one *Escherichia* sp., preferably *Escherichia coli*. The bacteriophage can include, for example, any one of Optium-212, Optium-719, and/or Optium-819.

In another aspect, the composition includes a plurality of bacteriophages. The plurality of bacteriophages can each have a narrow tropism and/or the plurality can have a collectively narrow tropism. In at least one aspect, the narrow tropism can be a similar or the same tropism. For instance, the plurality of bacteriophages can each target the same single, or narrow range of, bacterial genera and/or species or strain. Illustratively, the plurality of bacteriophages can be tropic for the same *Enterobacter* sp., preferably *Enterobacter cloacae*, more preferably *Enterobacter cloacae* strain B29. The bacteriophage can include, for example, any two or more of Optium-18, Optium-38, Optium-125, Optium-126, and Optium-712. Such compositions can be useful to target and reduce the concentration of, for example, the same *Enterobacter* sp. in the mammalian gut, preferably while not exhibiting cross reactivity with other bacterial genera and/or species or strain in the mammalian gut. Moreover, such compositions can be useful to target and kill the single, or narrow range of, bacterial genera and/or species or strain in the mammalian gut before the bacterium has time to adapt and/or develop resistance to any one or more of the plurality of bacteriophages.

In another aspect, the plurality of bacteriophages can be tropic for the same *Klebsiella* sp., preferably *Klebsiella pneumoniae*. The bacteriophages can include, for example, any two or more of Optium-12, Optium-79, and/or Optium-817.

In another aspect, the plurality of bacteriophages can be tropic for the same *Serratia* sp., preferably *Serratia marcescens*. The bacteriophages can include, for example, any two or more of Optium-148, Optium-155, Optium-162, and/or Optium-169.

In another aspect, the plurality of bacteriophages can be tropic for the same *Escherichia* sp., preferably *Escherichia coli*. The bacteriophages can include, for example, any two or more of Optium-212, Optium-719, and/or Optium-819.

In another aspect, the plurality of bacteriophages can each have narrow and different tropisms. For instance, the plurality of bacteriophages can each target a different single, or narrow range of, bacterial genera and/or species or strain. Such compositions can be useful to target and reduce the concentration of, for example, a plurality of bacterial genera and/or species or strain in the mammalian gut, preferably while not exhibiting cross reactivity with other bacterial genera and/or species or strain in the mammalian gut. Illustratively, the plurality of bacteriophages can each be tropic for a different single, or narrow range of, bacterial genera and/or species or strain and, collectively, be tropic for at least two bacterial genera and/or species or strain, preferably selected from *Enterobacter* sp., *Escherichia* sp., *Serratia* sp., and/or *Klebsiella* sp., more preferably selected from *Enterobacter cloacae*, preferably *Enterobacter cloacae* strain B29, *Escherichia coli*, *Serratia marcescens*, and/or *Klebsiella pneumoniae*.

Illustratively, the composition can include one or more bacteriophage selected from each of two or more groups of bacteriophage, the groups comprising (1) bacteriophage having tropism for the same *Enterobacter* sp., preferably *Enterobacter cloacae*, more preferably *Enterobacter cloacae* strain B29 and most preferably selected from any one or more of Optium-18, Optium-38, Optium-125, Optium-126, and Optium-712, (2) bacteriophage having tropism for the same *Klebsiella* sp., preferably *Klebsiella pneumoniae*, more preferably selected from any one or more of Optium-12, Optium-79, and/or Optium-817, (3) bacteriophage having tropism for the same *Serratia* sp., preferably *Serratia marcescens*, more preferably selected any one or more of Optium-148, Optium-155, Optium-162, and/or Optium-169, (4) bacteriophage having tropism for the same *Escherichia* sp., preferably *Escherichia coli*, more preferably selected from any one or more of Optium-212, Optium-719, and/or Optium-819. In some embodiments, the composition can include two or more bacteriophages selected from each of two or more of the above groups of bacteriophages. In some embodiments, the composition can include three or more bacteriophage selected from each of two or more the above groups of bacteriophages. Such compositions can be useful to target and kill the target bacterial genera and/or species or strain from each of the two or more groups in the mammalian gut before the bacteria have time to adapt and/or develop resistance to any one or more of the plurality of bacteriophages.

Illustratively, the composition can include one or more bacteriophage selected from each of three or more the above groups of bacteriophages. In some embodiments, the composition can include two or more bacteriophage selected from each of three or more the above groups of bacteriophages. In some embodiments, the composition can include three or more bacteriophage selected from each of three or more the above groups of bacteriophages. Such compositions can be useful to target and kill the target bacterial genera and/or species or strain from each of the three or more groups in the mammalian gut before the bacteria has time to adapt and/or develop resistance to any one or more of the plurality of bacteriophages.

Illustratively, the composition can include one or more bacteriophage selected from each of the four above groups of bacteriophages. In some embodiments, the composition can include two or more bacteriophage selected from each of the four above groups of bacteriophages. In some embodiments, the composition can include three or more bacteriophage selected from each of the four above groups of bacteriophages. Such compositions can be useful to target and kill the target bacterial genera and/or species or strain from each of the four above groups, in the mammalian gut, before the bacteria has time to adapt and/or develop resistance to any one or more of the plurality of bacteriophages.

In some embodiments, the bacteriophage is one or more of Optium-12, Optium-18, Optium-38, Optium-79, Optium-125, Optium-126, Optium-148, Optium-155, Optium-162, Optium-169, Optium-212, Optium-712, Optium-719, Optium-712 and/or Optium-819. In one exemplary embodiment, a composition includes each of bacteriophages Optium-12, Optium-18, Optium-38, Optium-79, Optium- 125, Optium-126, Optium-148, Optium-155, Optium-162, Optium-169, Optium-212, Optium-712, Optium-719, Optium-712 and/or Optium-819 that collectively have a narrow tropism for *Enterobacter cloacae, Escherichia coli, Serratia marcescens,* and/or *Klebsiella pneumoniae.*

In another aspect, the bacteriophage is tropic for at least one of *Enterobacter* sp., *Escherichia* sp., *Serratia* sp., *Klebsiella* sp., *Citrobacter* sp., *Kluyvera* sp., and/or *Yokenella* sp., preferably at least one of *Enterobacter cloacae, Escherichia coli, Serratia marcescens, Klebsiella pneumoniae, Enterobacter aerogenes, Kluyvera ascorbata, Citrobacter freundii,* and/or *Yokenella regensburgei.*

It should be appreciated that the bacterium *Enterobacter aerogenes* has recently been re-classified as *Klebsiella aerogenes,* and for the purposes of this disclosure, the bacterial species *Enterobacter aerogenes* is synonymous with *Klebsiella aerogenes.*

In some embodiments, the bacteriophages is one or more of Optium-12, Optium-17, Optium-18, Optium-24, Optium-27, Optium-34, Optium-35, Optium-38, Optium-46, Optium-67, Optium-79, Optium-82, Optium-86, Optium-88, Optium-113, Optium-116, Optium-117, Optium-118, Optium-121, Optium-125, Optium-126, Optium-148, Optium-155, Optium-162, Optium-169, Optium-212, Optium-219, Optium-225, Optium-304, Optium-356, Optium-417, Optium-502, Optium-531, Optium-574, Optium-688, Optium-712, Optium-716, Optium-719, Optium-747, Optium-812, Optium-817, Optium-819, Optium-835, and/or Optium-971 that collectively have a narrow tropism for *Enterobacter cloacae, Escherichia coli, Serratia marcescens, Klebsiella pneumoniae, Enterobacter aerogenes, Kluyvera ascorbata, Citrobacter freundii,* and/or *Yokenella regensburgei.*

For example, a composition of the present disclosure can include a plurality of bacteriophages that collectively have a narrow tropism for two or more obesogenic, inflammatory, and/or other bacteria. A first bacteriophage or set of bacteriophages can have a tropism for *Enterobacter* sp., preferably *Enterobacter cloacae,* more preferably *Enterobacter cloacae* strain B29. The first bacteriophage can be selected from the group consisting of Optium-18, Optium-38, Optium-125, Optium-126, and Optium-712. In some embodiments, the first bacteriophage is included within a first set of bacteriophages that includes at least one other bacteriophage selected from the group consisting of Optium-18, Optium-38, Optium-125, Optium-126, and Optium-712. In some embodiments, the first set of bacteriophages includes each of Optium-18, Optium-38, Optium-125, Optium-126, and Optium-712.

Alternatively, the first bacteriophage and/or first set of bacteriophages can have a tropism for *Escherichia* sp., preferably *Escherichia coli.* The first bacteriophage can be selected from the group consisting of Optium-212, Optium-719, and Optium-819. In some embodiments, the first bacteriophage is included within a first set of bacteriophages that includes at least one other bacteriophage selected from the group consisting of Optium-212, Optium-719, and Optium-819. In some embodiments, the first set of bacteriophages includes each of Optium-212, Optium-719, and Optium-819.

Alternatively, the first bacteriophage and/or first set of bacteriophages can have a tropism for *Serratia* sp., *Serratia marcescens.* The first bacteriophage can be selected from the group consisting of Optium-148, Optium-155, Optium-162, and Optium-169. In some embodiments, the first bacteriophage is included within a first set of bacteriophages that includes at least one other bacteriophage selected from the group consisting of Optium-148, Optium-155, Optium-162, and Optium-169. In some embodiments, the first set of bacteriophages includes each of Optium-148, Optium-155, Optium-162, and Optium-169.

Alternatively, the first bacteriophage and/or first set of bacteriophages can have a tropism for *Klebsiella* sp., preferably *Klebsiella pneumoniae.* The first bacteriophage can be selected from the group consisting of Optium-12, Optium-79, and Optium-817. In some embodiments, the first bacteriophage is included within a first set of bacteriophages that includes at least one other bacteriophage selected from the group consisting of Optium-12, Optium-79, and Optium-817. In some embodiments, the first set of bacteriophages includes each of Optium-12, Optium-79, and Optium-817.

The first bacteriophage and/or first set of bacteriophages can be included in a composition having a second bacteriophage and/or second set of bacteriophages having a tropism for at least one of *Enterobacter* sp., *Escherichia* sp., *Serratia* sp., and *Klebsiella* sp., preferably at least one of *Enterobacter cloacae, Escherichia coli, Serratia marcescens,* and *Klebsiella pneumoniae.*

In embodiments where the second bacteriophage and/or second set of bacteriophages is tropic for *Enterobacter* sp., preferably *Enterobacter cloacae,* the second bacteriophage can be any of Optium-18, Optium-38, Optium-125, Optium-126, and Optium-712. The second bacteriophage can additionally be included with a second set of bacteriophages that includes at least one other bacteriophage selected from Optium-18, Optium-38, Optium-125, Optium-126, and Optium-712. In some embodiments, the second set of bacteriophages includes each of Optium-18, Optium-38, Optium-125, Optium-126, and Optium-712.

In embodiments where the second bacteriophage and/or second set of bacteriophages is tropic for *Escherichia* sp., preferably *Escherichia coli,* the second bacteriophage can be any of Optium-212, Optium-719, and Optium-819. The second bacteriophage can additionally be included with a second set of bacteriophages that includes at least one other bacteriophage selected from Optium-212, Optium-719, and Optium-819. In some embodiments, the second set of bacteriophages includes each of Optium-212, Optium-719, and Optium-819.

In embodiments where the second bacteriophage and/or second set of bacteriophages is tropic for *Serratia* sp., preferably *Serratia marcescens,* the second bacteriophage can be any of Optium-148, Optium-155, Optium-162, and Optium-169. The second bacteriophage can additionally be included with a second set of bacteriophages that includes at least one other bacteriophage selected from Optium-148, Optium-155, Optium-162, and Optium-169. In some embodiments, the second set of bacteriophages includes each of Optium-148, Optium-155, Optium-162, and Optium-169.

In embodiments where the second bacteriophage and/or second set of bacteriophages is tropic for *Klebsiella* sp., preferably *Klebsiella pneumoniae,* the second bacteriophage can be any of Optium-12, Optium-79, and Optium-817. The second bacteriophage can additionally be included with a second set of bacteriophages that includes at least one other bacteriophage selected from Optium-12, Optium-79, and Optium-817. In some embodiments, the second set of bacteriophages includes each of Optium-12, Optium-79, and Optium-817.

It should be appreciated that upon selecting a second bacteriophage and/or second set of bacteriophages, the composition can additionally include a third and/or fourth bacteriophage or sets of bacteriophages. Each of the third and fourth bacteriophages or sets of bacteriophages can be selected from the remaining sets of bacteriophages tropic for *Enterobacter* sp., *Escherichia*, sp., *Serratia* sp., or *Klebsiella* sp., preferably *E. cloacae, E. coli, S. marcescens,* or *K. pneumoniae.*

In addition to the foregoing, the composition can include additional sets of bacteriophages having a tropism for additional obesogenic, inflammatory, and/or other bacteria. For example, the composition can include one or more bacteriophages tropic for *Enterobacter aerogenes,* including any (or all) of Optium-27, Optium-35, Optium-82, Optium-688 Optium-747, and Optium-971. Additionally, or alternatively, the composition can include one or more bacteriophages tropic for *Kluyvera* sp., preferably *Kluyvera ascorbata,* including any (or all) of Optium-67, Optium-121, Optium-502, and Optium-531. Additionally, or alternatively, the composition can include one or more bacteriophages tropic for *Citrobacter* sp., preferably *Citrobacter freundii,* including any (or all) of Optium-24, Optium-117, Optium-219, Optium-225 Optium-574, and Optium-716. Additionally, or alternatively, the composition can include one or more bacteriophages tropic for *Yokenella* sp., preferably *Yokenella regensburgei,* including any (or all) of Optium-46, Optium-116, Optium-304, Optium-356, Optium-812, and Optium-835.

In some embodiments, the composition includes only one bacteriophage or a plurality of bacteriophages selected from Optium-24, Optium-27, Optium-35, Optium-46, Optium-67, Optium-82, Optium-116, Optium-117, Optium-121, Optium-219, Optium-225, Optium-304, Optium-356, Optium-502, Optium-531, Optium-574, Optium-688, Optium-716, Optium-747, Optium-812, Optium-835, and Optium-971.

The number and type of phage included within the composition may vary according to the application and obesogenic, inflammatory, and/or other bacteria to be targeted. In some embodiments, the composition includes at least two, preferably 3-5 bacteriophages having a tropism for the same target bacteria. Having more than one bacteriophage specific for a given bacterium can beneficially increase the effectiveness of the composition. The tropism for at least some of the bacteriophages disclosed herein is illustrated in FIG. 3. In some instances, an illustration of tropism such as that shown in FIG. 3 can be helpful in selecting the number and type of phages to include in a composition having a single bacteriophage or cocktail of bacteriophages. For example, a minimum (or smaller number) of phages can be selected based on their overlapping tropism such that at least two, preferably 3-5 phages, are tropic for each of the target bacteria.

In a preferred embodiment, the bacteriophages are additionally selected for those with greater genetic diversity from each other and/or for the mode of attachment or infection. Targeting the same bacterium with a plurality of genetically diverse phages and/or phages having different modes of attachment or infection can beneficially reduce the likelihood of escape mutants within the bacterial populations.

It should be appreciated that the bacteriophages included in the composition can be selected de novo in addition to and/or complementary with the foregoing and can be selected for a narrow tropism against any target obesogenic, inflammatory, and/or other bacteria. Such identification and selection can be undertaken, for example, using the disclosed processes for making the disclosed compositions.

Alternatively, or in addition, the bacteriophage can be classified or typed as, or have a classification (or type) selected from the group consisting of: Myoviridae, preferably (i) T4-like, more preferably subcluster G, I, or a new or unknown subcluster type, or (ii) RV5-like, more preferably subcluster C or a new or unknown subcluster type; Podoviridae, preferably T7-like, more preferably subcluster B or a new or unknown subcluster type; Siphoviridae, preferably (i) S01-like, more preferably subcluster A or a new or unknown subcluster type, (ii) 9g-like, more preferably subcluster B or a new or unknown subcluster type, (iii) T1-like, more preferably subcluster B, D, or a new or unknown subcluster type; Jello cluster, preferably subcluster A, B, or a new or unknown subcluster type; FaintSaint cluster; and Phage T1-like. Table 1 (below) illustrates various classifications for 15 separate bacteriophages of the present disclosure. Additional bacteriophages of the present disclosure can be similarly classified.

TABLE 1

Possible Classification of Various Disclosed Bacteriophages

| Bacterial Target | Phage Name | Classification |
| --- | --- | --- |
| *Enterobacter cloacae* | Opt-18 | Myoviridae, T4-like subcluster I |
| | Opt-38 | unknown |
| | Opt-125 | Myoviridae, T4-like subcluster G |
| | Opt-126 | Myoviridae, T4-like |
| | Opt-712 | Podoviridae, T7-like |
| *Escherichia coli* | Opt-212 | Siphoviridae, SO1-like subcluster A |
| | Opt-719 | Siphoviridae, 9g-like subcluster B |
| | Opt-819 | Myoviridae, RV5-like subcluster C |
| *Klebsiella pneumoniae* | Opt-12 | Podoviridae, T7-like subcluster B |
| | Opt-79 | Siphoviridae, T1-like subcluster B |
| | Opt-817 | Siphoviridae, T1-like subcluster D |
| *Serratia marcescens* | Opt-148 | Jello Cluster, subcluster A |
| | Opt-155 | FaintSaint cluster |
| | Opt-162 | Jello Cluster, subcluster B |
| | Opt-169 | Phage T1-like |

Testing shows that each of the bacteriophages listed in Table 1, above (see column 2—Phage Name) and further, each of the bacteriophages listed in FIG. 3 (see column 2—Phage Name) have, exhibit, and/or possess (i) the ability to successfully specifically target, infect, and kill (e.g., lyse) their corresponding bacterial host target(s) (see column 1—Bacterial Target) and, in some instances, (ii) a narrow tropism for said target(s) (with little or no significant cross reactivity with other host targets listed in Table 1, FIG. 3, and/or common to the mammalian and/or human gut (microbiome). See FIG. 3. Where a first bacteriophage exhibits a narrow tropism for a single host bacterium, said first bacteriophage can be useful for highly specific targeting and killing of said single bacterium, whether used (e.g., administered) alone or in combination with one or more additional bacteriophage. The one or more additional bacteriophage can have (i) the same or (ii) a different narrow tropism (e.g., a specific infectivity for the same, single bacterial host or a different single bacterial host). Alternatively, the one or more additional bacteriophage can have tropism broader than the tropism of said first bacteriophage (e.g., a specific infectivity for a range of bacterial hosts, which may or may not include the bacterial host of the first bacteriophage).

Where the first bacteriophage exhibits broad tropism for a plurality of host bacterial hosts, said first bacteriophage can be useful for broad targeting and killing of said plurality host bacterial hosts, whether used (e.g., administered) alone or in combination with one or more additional bacteriophage. The one or more additional bacteriophage can have (i) the same or (ii) a different broad tropism (e.g., a specific infectivity for the same plurality of bacterial hosts or other than the plurality of bacterial hosts). Alternatively, the one or more additional bacteriophage can have narrow tropism for a single or narrower range of bacterial hosts. In each case, each of the bacteriophage listed in FIG. 3, for example, can be useful (e.g., as a component of a composition for administration to a mammalian, preferably human, subject) alone or in combination with any one or more of the other bacteriophage listed in FIG. 3, for example.

In some embodiments, a targeted therapeutic can be developed, prescribed and/or administered to treat a specific combination of (potentially harmful or detrimental) bacteria in the gut microbiome of the subject. Alternatively, a composition that comprises a standard or universal cocktail (or mixture) of phage, which, collectively, target and kill any of a variety of (potentially harmful or detrimental) bacteria that may be present in the gut microbiome of the subject, can be developed, prescribed and/or administered.

The tropism for each bacteriophage listed in Table 3 was determined using a lytic activity assay, as described, for example, in Example 4 below, where the respective bacteriophage was combined with a culture of the specific target microbe. Aliquots of the culture over time were plated to determine the (degree of) presence or absence of the bacterium over time. A reduced bacterial titer corresponded with the bacteriophage being tropic for and killing the bacterium. For example, as shown in FIG. 4A-4I, each of Optium-125, Optium-417, Optium-18, Optium-118, Optium-86, Optium-712, Optium-113, Optium-34, and Optium-38, respectively, was analyzed using a lytic activity assay, and as shown in FIGS. 4A-4I, the phages were able to infect and lyse *Enterobacter cloacae*, specifically strain B29. This demonstrates both the phages' lytic capacity and tropism for the given target bacterium. It should be appreciated that the lytic activity assay is one method for characterizing the lytic activity and/or tropism for identified phages, but other methods and assays exist and are known in the art that can be used in addition to or alternatively from the plaque-based assay. For example, a plaque assay or spot assay could be used.

The bacteriophages incorporated into compositions of the present disclosure preferably do not have genes encoding bacterial toxins that may negatively affect a human, such as, for example, cholerae toxin, botulinum toxin, and diphtheria toxin. Additionally, the bacteriophage is preferably devoid of any gene encoding a bacterial virulence factor or phage integrase genes. This can beneficially prevent the bacteriophage from delivering a virulence factor to its host bacterium, which could then cause a non-pathogen or opportunistic pathogen to become virulent.

The bacteriophages of various embodiments may include mutant or recombinant strains of an isolated bacteriophage capable of infecting and lysing the obesogenic, inflammatory, and/or other bacterium. The mutant of various embodiments can be prepared, for example, by exposing an isolated bacteriophage to a mutagenic agent such as a chemical mutagen or electromagnetic radiation. Recombinant bacteriophage strains of various embodiments can be prepared by inserting a polynucleotide into the genome of the isolated bacteriophage strain, where the polynucleotide encodes for an antibacterial protein or therapeutic protein. Examples of antibacterial and therapeutic proteins are disclosed in PCT Application Publication No. WO 2018/174810 and WO 2018/030323, the disclosures of which are incorporated in its entirety by reference herein.

As discussed above, the compositions of the present disclosure include bacteriophages that, when administered to a mammal, preferably a human, decrease the number or concentration of obesogenic, inflammatory, and/or other bacteria within the intestinal microbiome of the mammal. The compositions disclosed herein can be included within a kit that additionally includes a probiotic and/or prebiotic. Alone, a probiotic may not be as effective or have as much of a beneficial effect when the bacteria within the probiotic have to compete with native bacteria in the gut. However, when coupled with and co-administered with the compositions disclosed herein, the disclosed probiotics can beneficially improve and/or stabilize the gut microbiome and provide a healthier and often more diverse microbiome. This may be due, at least in part, to the bacteriophages within the composition clearing niches within the gut previously held by the targeted bacteria. The probiotic microbes can then colonize the newly clearly niches throughout the gut and thereby provide a twofold benefit: preventing the recolonization of obesogenic, inflammatory, and/or other bacteria by occupying the newly cleared niches and providing the host with beneficial nutrients and/or metabolites.

In one embodiment, the probiotic includes a plurality of bacteria selected from *Bifidobacterium* sp. and *Lactobacillus* sp. For example, a probiotic of the present disclosure can include any (or all) of *Lactobacillus acidophilus, Lactobacillus brevis, Lactobacillus* casei, *Lactobacillus salivarius, Lactobacillus lactis, Bifidobacterium bifidum*, and/or *Bifidobacterium lactis*.

In addition to, or alternatively from, the foregoing bacterial strains, the priobiotic can include any (or all) of *Lactobacillus rhamnosus, Lactobacillus reuteri, Bacteroides fragilis, Bifidobacterium breve, Bifidobacterium longum*, and/or *Bifidobacterium pseudocatenulatum*. In some embodiments, the priobiotic can additionally include one of, a plurality of, or all of: *Bifidobacterium infantis, Lactobacillus plantarum, Lactobacillus delbrueckii, Lactobacillus bulgaricus, Lactococcus cremoris*, and/or *Enterococcus faecium*.

In addition to, or alternatively from, the foregoing bacterial strains, the priobiotic can include any (or all) of *Roseburia hominis, Akkermansia muciniphila*, or *Faecalibacterium prausnitzii*. Additionally, or alternatively, the probiotic can include one or more bacterium of the Lachnospiraceae family.

Formulation and Dosage of Compositions

As provided above, each of the disclosed compositions includes a pharmaceutically-acceptable carrier in addition to one or more bacteriophages having a narrow tropism for one or more obesogenic, inflammatory, and/or other bacterium. As used herein the term "pharmaceutically acceptable" means a biologically compatible formulation, gaseous, liquid or solid, or mixture thereof, that is suitable for one or more routes of administration, in vivo delivery, or contact. A formulation is compatible in that it does not destroy activity of an active ingredient therein (e.g., the bacteriophage or bacteriophage cocktail) or induce adverse side effects that outweigh any prophylactic or therapeutic effect or benefit.

It should be appreciated that the disclosed compositions may contain one or more (pharmaceutically-acceptable) carriers or excipients. Pharmaceutically acceptable carriers and excipients (or the pharmaceutical acceptability thereof) are determined in part by the particular composition being administered, as well as by the particular method used to administer the composition. Accordingly, there exists a wide variety of suitable formulations of pharmaceutical compositions (see, e.g., Remington's Pharmaceutical Sciences, incorporated herein by reference).

Suitable excipients may be or include carrier molecules and can include antioxidants such as ascorbic acid; chelating agents such as EDTA; carbohydrates such as dextrin, hydroxyalkylcellulose, hydroxyalkylmethylcellulose, and stearic acid; liquids such as oils, water, saline, glycerol and ethanol; wetting or emulsifying agents; pH buffering substances; and the like. Liposomes are also included within the definition of pharmaceutically acceptable excipients.

Additional or alternative examples of carriers include silicon dioxide (silica, silica gel), carbohydrates or carbohydrate polymers (polysaccharides), cyclodextrins, starches, degraded starches (starch hydrolysates), chemically or physically modified starches, modified celluloses, gum arabic, ghatti gum, tragacanth, karaya, carrageenan, guar gum, locust bean gum, alginates, pectin, inulin or xanthan gum, or hydrolysates of maltodextrins. In various embodiments, the bacteriophage can be dispersed throughout the carrier. In various embodiments, the pharmaceutically acceptable excipient or carrier can be suitable for oral consumption.

The compositions described herein may be formulated in any form suitable for the intended method of administration. When intended for oral use, for example, tablets, troches, lozenges, aqueous or oil suspensions, non-aqueous solutions, dispersible powders or granules (including micronized particles or nanoparticles), emulsions, hard or soft capsules, syrups, or elixirs may be prepared. Orally consumable products can also include a semi-solid food, solid food, a semi-solid or solid spoonable food, confectionary, drink, or dairy product. The dairy product of various embodiments is ice cream, milk, milk powder, yogurt, kefir, or quark. Compositions intended for oral use may be prepared according to any method known to the art for the manufacture of pharmaceutical compositions, and such compositions may contain one or more agents including sweetening agents, flavoring agents, coloring agents, and preserving agents to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin, or acacia; and lubricating agents, such as magnesium stearate, stearic acid, or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing, or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g., dextran sulfate); glycoaminoglycans and glycosaminoglycan-like compounds (e.g., hyaluronic acid); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters, or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol, or sucrose. Such formulations may also contain a demulcent, a preservative, a flavoring, or a coloring agent.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

It should be appreciated that the compositions and/or formulations disclosed herein contain a total amount of one or more bacteriophages (collectively or individually) sufficient to achieve the intended effect (e.g., reduce the number or concentration of obesogenic, inflammatory, and/or other bacteria in the intestinal microbiome of the subject).

The compositions may, for convenience, be prepared or provided as a unit dosage form and can be packaged in unit dosage forms for ease of administration and uniformity of dosage. A "unit dosage form" as used herein refers to a physically discrete unit suited as unitary dosages for the subject to be treated. Each unit containing a predetermined quantity of the one or more bacteriophage optionally in association with a pharmaceutically-acceptable carrier (e.g., excipient, diluent, vehicle or filling agent) which, when administered in one or more doses, is calculated to produce the desired effect (e.g., reduce the number or concentration of obesogenic, inflammatory, and/or other bacteria in the intestinal microbiome of the subject). Unit dosage forms can contain a daily dose or unit, daily sub-dose, or an appropriate fraction thereof, of an administered compound. Unit dosage forms also include, for example, capsules, troches, cachets, lozenges, tablets, ampules and vials, which may include a composition in a freeze-dried or lyophilized state. A sterile liquid carrier, for example, can be added prior to administration or delivery in vivo. Unit dosage forms additionally include, for example, ampules and vials with liquid compositions disposed therein. The individual unit dosage forms can be included in multi-dose kits or containers.

A dosage (or administration) of the composition can one or more doses. A dose of the composition can include, for example, greater than or equal to $1 \times 10^4$ PFU/mL or PFU/mg of composition of one or more bacteriophage, in accordance with one or more aspects or embodiments of the present disclosure. Alternative doses can include greater than or equal to $1 \times 10^5$, $1 \times 10^6$, $1 \times 10^7$, $1 \times 10^8$, $1 \times 10^9$, or $1 \times 10^{10}$ PFU/mL or PFU/mg. Suitable dosage size or amounts can range from 1 µL to 500 mL or more (e.g., of fluid or semi-solid composition), 1 µg to 5000 mg or more (e.g., of solid or semi-solid composition), or other amount as known in the art.

The disclosed compositions can be administered in accordance with the methods at any frequency as a single bolus or multiple dose e.g., one, two, three, four, five, or more times hourly, daily, or weekly or for as long as appropriate. Exemplary frequencies are typically from 1-3 times, 2-times or once, daily; for example, once per day for 30 days or indefinitely. Timing of administration can be dictated by the desired physiological characteristic to be affected, such as decreasing or inducing weight loss, decreasing inflammation, etc. The skilled artisan will appreciate the factors that may influence the dosage, frequency, and timing required to provide an amount sufficient or effective for providing the desired effect or benefit. Dosage and administration can be adjusted to provide sufficient levels of the one or more bacteriophage (collectively or individually) or to maintain the desired effect.

In at least one embodiment, the composition can be administered or received as part of a treatment protocol. The treatment protocol can include a first treatment period (or phase). The first treatment phase can include a first dosage of the composition, administered or received in accordance with a first dosage schedule. The first dosage schedule can be, for example, a daily dosage schedule or any other suitable dosage schedule (e.g., twice daily, every other day, once weekly, twice weekly, etc.). The first dosage can include any suitable dose (amount) disclosed herein. In at least one embodiment, the first dose (amount) of the first dosage in the first treatment phase can be or include a (relatively high) initial treatment dose (e.g., greater than or equal to $1 \times 10^6$, $1 \times 10^7$, $1 \times 10^8$, $1 \times 10^9$, or $1 \times 10^{10}$ PFU/mL or PFU/mg. In some embodiments, the first dosage phase (or schedule thereof) can be or last for any suitable amount of time (e.g., greater than or equal to 1 week, 2 weeks, 3 weeks, 4 weeks, 1 month, 2 months, 3 months, 6 months, 9 months 1 year, etc.).

In some embodiments, the treatment protocol can include a second treatment period (or phase). The second treatment phase can include a second dosage of the composition, administered or received in accordance with a second dosage schedule. The second dosage schedule can be, for example, a weekly dosage schedule or any other suitable dosage schedule (e.g., daily, every other day, twice weekly, etc.). The second dosage can include any suitable dose (amount) disclosed herein. In at least one embodiment, the second treatment phase can include a (lower) maintenance treatment dose (e.g., greater than or equal to $1 \times 10^4$, $1 \times 10^5$, $1 \times 10^6$, $1 \times 10^7$, or $1 \times 10^8$ PFU/mL or PFU/mg. Illustratively, the second dosage can include a lower concentration of phage that the first dosage. Alternatively, or in addition, the second treatment phase can include a less frequent dosage schedule than the first treatment phase. In some embodiments, the second dosage phase (or schedule thereof) can be or last for any suitable amount of time (e.g., greater than or equal to 3 months, 6 months, 9 months, 1 year, 2 years, 3 years, etc., or indefinitely).

In some embodiments, a composition containing one or more bacteriophages is co-administered with a probiotic and/or prebiotic.

As used herein, "co-administration" means concurrently or administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers. In some embodiments, co-administration is concurrent administration.

Processes and Methods for Making and Administering Compositions

Embodiments of the present disclosure additionally include processes for making the compositions disclosed herein and methods for administering said compositions to decrease the number or concentration of obesogenic, inflammatory, and/or other bacteria in the intestinal microbiome of a mammal, preferably a human.

An exemplary process for preparing the bacteriophage component of compositions disclosed herein, includes isolating the bacteriophage from an environmental source and characterizing the bacteriophage. An exemplary, detailed process is provided in Example 3 below.

In general, "characterizing" the bacteriophage consists of measuring its lytic activity to ensure that the bacteriophage is a lytic phage and not a lysogenic phage, measuring the host range to ensure the phage has a narrow tropism that includes a desired bacterial target, passing it through mice to ensure that the bacteriophage survives conditions of the mammalian gastrointestinal tract, and sequencing the bacteriophage genome to ensure that the phage is not harboring any bacterial toxin or virulence factor or integrase gene, which may indicate that the phage can be lysogenic. During the characterizing process, any bacteriophage that fails any one criterion is excluded from further consideration.

In some embodiments, genomic sequencing of the bacteriophage is performed to determine how closely related each of the various phages are, particularly when those phages are tropic for the same bacterium. This additional, sometimes optional step, can beneficially allow for the selection and combination of phages that are as unrelated to each other as possible and to decrease the likelihood that the targeted bacteria can develop resistance against the selected phages. Thus, after identifying and characterizing a first bacteriophage, additional phages specific for each additional putative obesogenic, inflammatory, and/or other bacterium can be included that are each validated as lytic, having a narrow and specific tropism, able to survive conditions in the mammalian GI tract, and unlikely to promote bacterial escape mutants resistant to the cocktail of phages.

Following isolation and characterization, the selected bacteriophage is prepared in any manner to be incorporated as a component of a food stuff, feed additive, or liquid additive and can be in various forms such as, for example, a liquid state or a dried state including as a powder. In other examples, the bacteriophage is dried by air drying method, natural drying method, a spray drying method, a freeze-drying method, or the like. The preparation of the bacteriophage strain can also serve to enhance the properties of the composition including stability. The term "foodstuff" is understood to be any substance or product which in the processed, partially processed, or unprocessed state are intended to be, or reasonably expected to be, ingested by humans. "Foodstuff" can also include drinks, chewing gum, and any substance—including water—intentionally added to the foodstuff during its manufacture, preparation or treatment. The term "feed" is understood to cover all forms of animal food. Foodstuffs can also be used as feeds.

In various embodiments, the bacteriophage is prepared in any manner to be incorporated as a component of a nutritional supplement to promote or support weight management and control, support metabolic health, and/or support a healthy balance in the gut microbiota, and can be in various forms such as, for example, a liquid state or a dried state including a powder. The term "nutritional supplement" is understood to cover substances or substance compositions which are intended as agents having properties to support or promote health, but not to treat, diagnose, prevent, or cure any disease.

As discussed above, the compositions disclosed herein can be administered alone or co-administered with a probiotic. The administration dosage and schedule can be determined based on the desired effect and as known in the art.

Abbreviated List of Defined Terms

To assist in understanding the scope and content of the foregoing and forthcoming written description and appended claims, a select few terms are defined directly below. Unless defined otherwise, all technical and scientific terms used herein have the same meaning as commonly understood by one of ordinary skill in the art to which the present disclosure pertains.

The terms "bacteriophage" or "phage," as used herein, includes any prokaryotic virus, preferably lytic viruses, that infect and kill bacteria. "Bacteriophage" and "phage" are used interchangeably and can include naturally-occurring and recombinant bacteriophages, unless otherwise indicated. A "naturally-occurring" bacteriophage is a phage isolated from a natural or human-made environment that has not been modified by genetic engineering. A "recombinant bacteriophage" is a phage that comprises a genome that has been genetically modified by insertion of a heterologous nucleic acid sequence into the genome or by removal of a nucleic acid sequence from the genome. The genome of a naturally-occurring phage may be modified by recombinant DNA technology to introduce a heterologous nucleic acid sequence into the genome at a defined site. Additionally, or alternatively, the genome of a naturally-occurring phage may be modified by recombinant DNA technology to remove nucleic acid sequences that, for example, encode bacterial virulence factors (e.g., toxins). A further description of bacteriophages can be found in U.S. Pat. No. 9,617,522, the entirety of which is incorporated by reference herein.

The term "co-administration" and similar terms refer to concurrent, sequential, and/or combined administration of two or more components. For instance, two components can be co-administered by administering each component in a separate dosage concurrently, simultaneously, or sequentially (e.g., distinct administrations separated by a period of time). The period of time can be very short (e.g., substantially immediately following a first administration) or it may be longer (e.g., 10-60 seconds later, 1-60 minutes later, 1-24 hours later, 1-7 days later, or any value or range of values therebetween). Concurrent or simultaneous administration can include overlapping administration timeframes for the two or more components or administration of a combination product comprising a mixture of the two or more components.

As used herein, the term "cocktail," "bacteriophage cocktail, "phage cocktail," or similar is intended to be understood as a composition that includes two or more bacteriophages. The composition may have a proportional or disproportional number or concentration of phages, and the phages comprising the cocktail may have overlapping or non-overlapping tropisms. The cocktail can be in a dry form or suspended in a pharmaceutically-acceptable carrier.

The term "gut," as used herein, is synonymous with "digestive tract," "gastrointestinal tract," or similar and is intended to include the system of modified epithelial cells, mucus, and associated environment and secreted factors spanning between the mammalian mouth and anus, including the intervening organs (e.g., stomach, small intestine, and large intestine).

The term "microbiome" may refer generally to the collective genomes of the microbiota or to the microorganisms themselves and may be used synonymously with the term microbiota.

The term "microbiota" generally refers to the population, collection, and/or totality of microbes in a defined environment, habitat, or ecological community, and typically includes a plurality of genera, species, or strains of commensal, symbiotic, beneficial, and/or opportunistic pathogenic microorganisms (e.g., bacteria, archaea, fungae, protists, and/or viruses), and typically including their genetic elements (genomes). For example, as used herein, the term "microbiota" or "microbiome" is generally made with reference to the population of microbes inhabiting the intestinal tract of a mammal (i.e. the intestinal microbiome).

The term "narrow host range," as used herein, particularly with respect to the tropism of a given bacteriophage, The term "obesogenic bacterium," "obesogenic bacteria," or similar term is intended to encompass those bacteria whose presence, concentration, or imbalance within the intestinal microbiome of a mammalian subject, preferably humans, correlate with, promote, or induce weight gain in the mammalian subject and/or whose removal or reduction within the intestinal microbiome of a mammalian subject, preferably humans, correlate with, promote, or induce weight loss in the mammalian subject. For example, a bacterium within the intestinal microbiome of a mammalian subject may be understood to be an obesogenic bacterium if when targeted by a specific bacteriophage (e.g., via administration of a tropic phage or phage cocktail), a concomitant reduction in the concentration of the bacterium correlates with, promotes, or induces weight loss in the mammalian subject (e.g., over time).

The term "inflammatory bacterium," "inflammatory bacteria," or similar term is intended to encompass those bacteria whose presence, concentration, or imbalance within the intestinal microbiome of a mammalian subject, preferably humans, correlates with, promotes, or induces inflammation, preferably low-level, systemic inflammation in the mammalian subject and/or whose removal or reduction within the intestinal microbiome of a mammalian subject, preferably humans, correlates with, promotes, or induces a decrease in such inflammation and/or inflammatory markers in the mammalian subject. For example, a bacterium within the intestinal microbiome of a mammalian subject may be understood to be an inflammatory bacterium if, when targeted by a specific bacteriophage (e.g., via administration of a narrowly tropic phage or phage cocktail), a concomitant reduction in the concentration of the bacterium correlates with, promotes, or induces a decrease in (low-level systemic) inflammation and/or inflammatory markers in the mammalian subject (e.g., over time).

The term "prebiotic" generally refers to a component (e.g., an energy source or food, food ingredient, dietary supplement, etc.) that when consumed by a mammalian subject stimulates the growth, diversity, or activity of at least a subset of microbes within the subject's microbiome. In some instances, the prebiotic can be selected to include a preferred food source for one or more bacteria within the subject's intestinal microbiome and/or within a co-administered probiotic to encourage the growth or activity of that population of microbes.

The term "probiotic" generally refers to one or more live microbes associated with neutral or beneficial effects in the mammalian gastrointestinal tract. An exemplary probiotic can include one or more of *Lactobacillus* sp., *Bifidobacterium* sp., *Saccharomyces* sp., and/or a component (e.g., a food, food ingredient, dietary supplement, etc.) that includes the same. Typically, when consumed, a probiotic can assist in maintaining or restoring beneficial levels, diversity, or activity, of the microbiome.

The terms "sequence identity" or "identity" refers to a specified percentage of residues in two nucleic acid or amino acid sequences that are identical when aligned for maximum correspondence over a specified comparison window, as measured by sequence comparison algorithms or by visual inspection. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity.

The term "subject," as used herein, is synonymous with the terms "patient," "individual," and similar terms, and generally refers to individual or organism of any mammalian species, (1) preferably including humans, whether or not under the care of a healthcare provider (e.g., a physician, nurse, or medical assistant or volunteer), and (ii) non-human mammals, whether or not under the care of a veterinarian or other veterinary professional, assistant, or volunteer, such as, but not limited to, dogs, cats, horses, cattle, rodents, or other domesticated or wild mammal.

Sequence Listing Table

For convenience, Table 2 (below) includes a list of each sequenced bacteriophage with its corresponding SEQ ID NO.

TABLE 2

SEQ ID NO Listing

| SEQ ID NO. | Optium Phage Name |
|---|---|
| SEQ ID NO. 1 | Optium-12 |
| SEQ ID NO. 2 | Optium-18 |
| SEQ ID NO. 3 | Optium-38 |
| SEQ ID NO. 4 | Optium-79 |
| SEQ ID NO. 5 | Optium-125 |
| SEQ ID NO. 6 | Optium-126 |
| SEQ ID NO. 7 | Optium-148 |
| SEQ ID NO. 8 | Optium-155 |
| SEQ ID NO. 9 | Optium-162 |
| SEQ ID NO. 10 | Optium-169 |
| SEQ ID NO. 11 | Optium-712 |
| SEQ ID NO. 12 | Optium-212 |
| SEQ ID NO. 13 | Optium-719 |
| SEQ ID NO. 14 | Optium-817 |
| SEQ ID NO. 15 | Optium-819 |
| SEQ ID NO. 16 | Optium-34 |
| SEQ ID NO. 17 | Optium-113 |
| SEQ ID NO. 18 | Optium-118 |
| SEQ ID NO. 19 | Optium-417 |

EXAMPLES

Example 1

FIG. 1 is a graphical representation showing improved oral glucose tolerance in mice with intestinal microbiotas colonized with *Enterobacter cloacae* strain B29 treated with bacteriophages as compared to control mice with intestinal microbiotas colonized with *Enterobacter cloacae* strain B29 but not treated with bacteriophages. As shown in FIG. 1, the phage cocktail inhibits B29-induced glucose intolerance. Prior to colonization with the human pathogen *E. cloacae* strain B29, mice are treated with oral antibiotics to deplete their native gut microbiota.

During week 1, all mice receive daily doses of B29 by oral gavage and are placed on a high fat diet (60% of total energy from fat, 20% from carbohydrates, and 20% from protein) to induce weigh gain. During week 2, the treatment group (dashed line) receives 7 daily doses of phage cocktail by oral gavage. During weeks 3-8, the treatment group (black line) receives bacteriophages in drinking water. The bacteriophage cocktail included greater than or equal to $1\times10^9$ PFU of Optium-125, Optium-417, Optium-18, Optium-118, Optium-86, Optium-712, Optium-113, Optium-34, and Optium-38.

The oral glucose tolerance test was performed at the end of week 8 by administering a glucose solution by oral gavage and monitoring blood glucose levels at the indicated time points over the next 2 hours. Blood sugar levels are significantly improved in the phage-treated group ($p<0.05$).

Example 2

A four-week test/trial was conducted using 17 individuals (10 male and 7 female) between the ages of 25 and 59 years old taking a single daily dose of a bacteriophage cocktail. The cocktail included greater than or equal to $1\times10^8$ PFU of Optium-12, Optium-18, Optium-38, Optium-79, Optium-125, Optium-126, Optium-212, Optium-712, Optium-719, Optium-712 and Optium-819, having a combined tropism for *Enterobacter cloacae, Escherichia coli,* and *Klebsiella pneumoniae*. Prior to inclusion within the composition, each bacteriophage was isolated at a titer greater than or equal to $1.0\times10^9$ phages.

Blood samples were taken from the participants and tests were performed before and after the four-week period. Blood tests showed statistically significant improvements in the reduction of inflammation, reduction in body weight and Body Mass Index (BMI), and an increase in high-density lipoprotein (HDL) cholesterol.

Figure 2A:
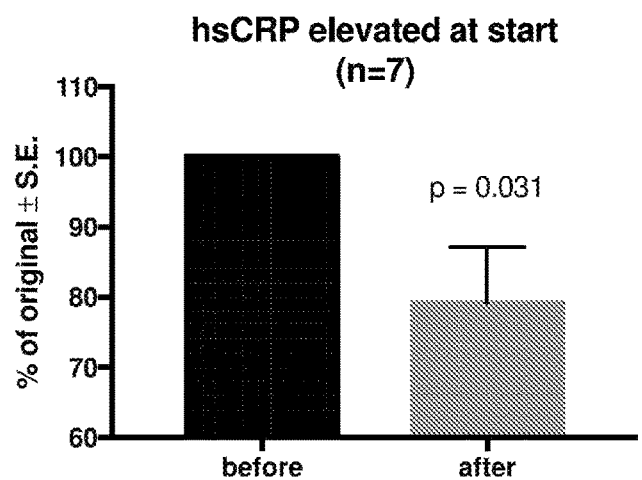
FIGS. 2A-2I illustrate results from a four-week trial of 17 individuals taking a single daily dose of a composition comprising a bacteriophage cocktail co-administered with a probiotic.
Figure 2B:
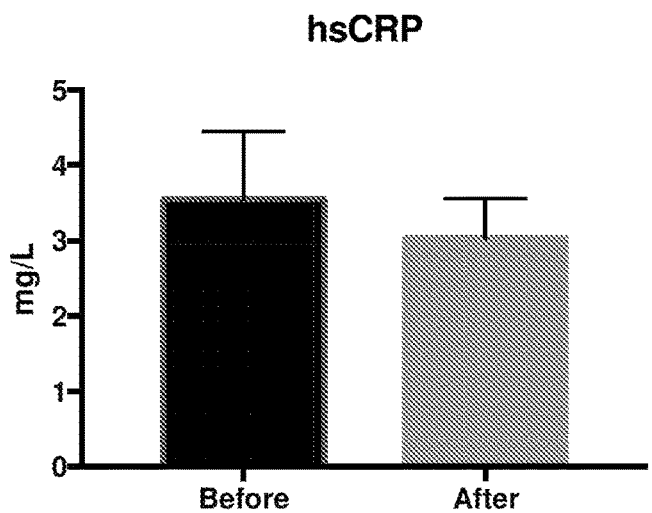
Figure 2C:
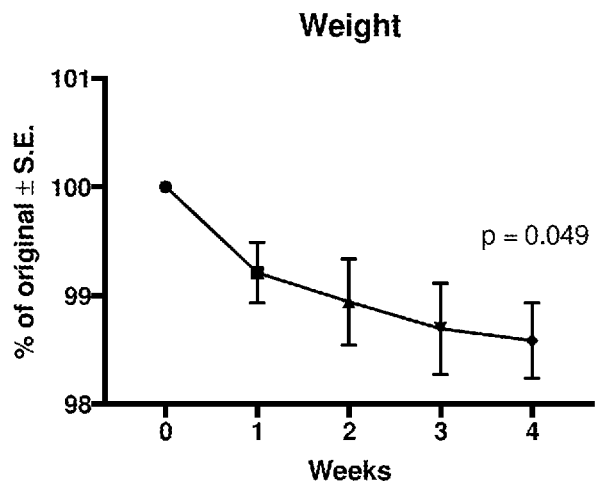
Figure 2D:
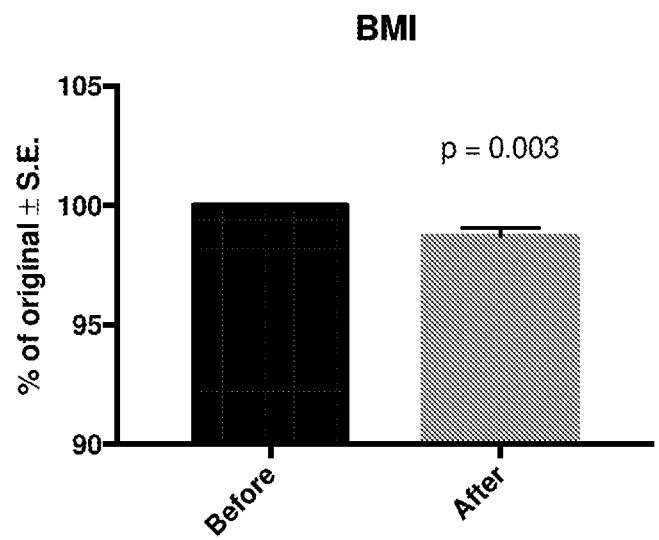
Figure 2E:
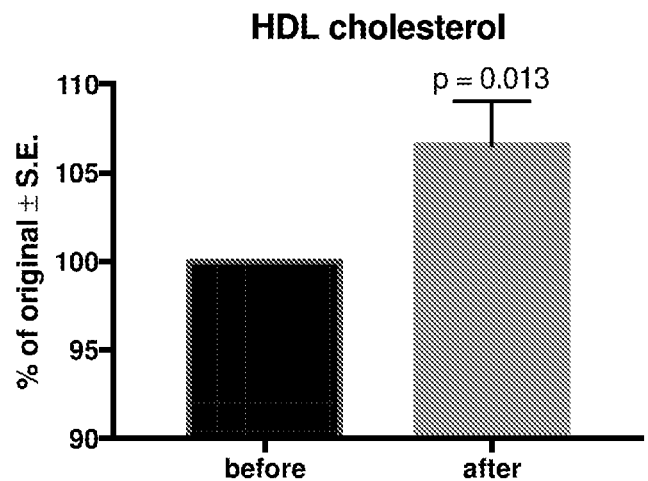
Figure 2F:
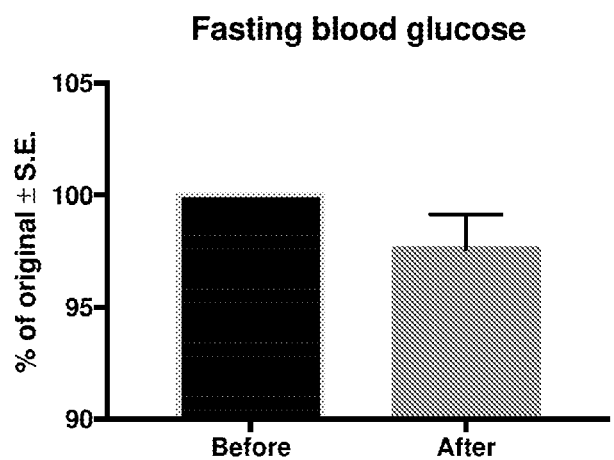
Figure 2G:
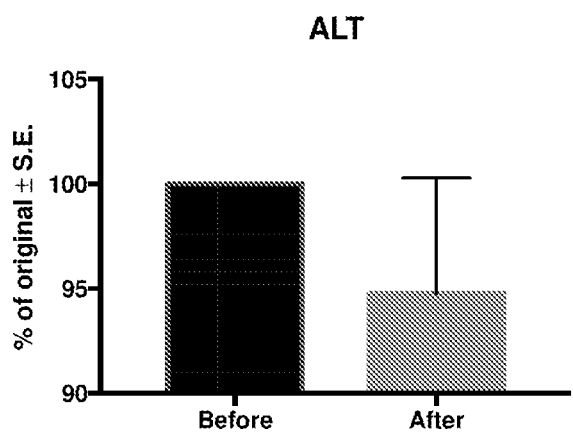
Figure 2H:
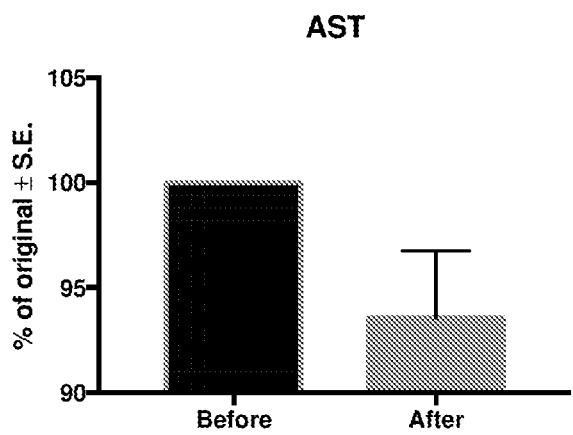
Figure 2I:
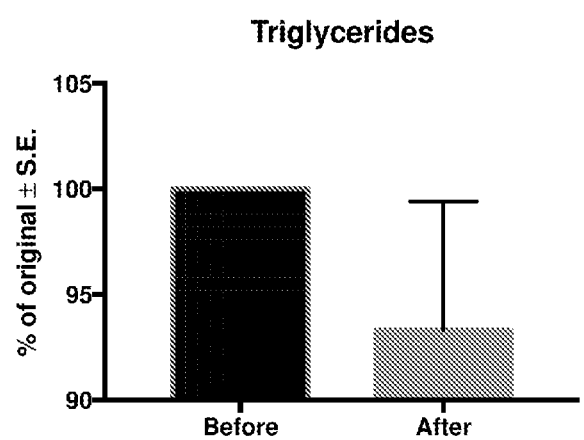
Figure 4A:
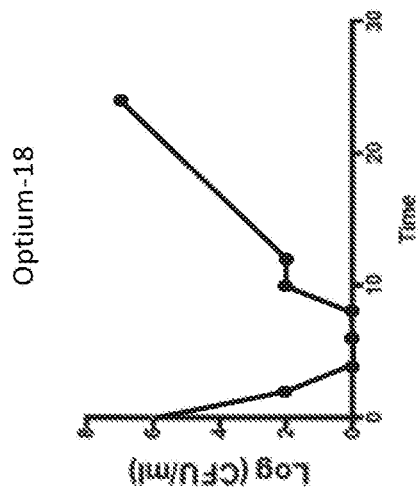
FIG. 4A-4I illustrate graphical representations showing lytic activity and tropism of different bacteriophage strains for *Enterobacter cloacae* strain B29.
Figure 4B:
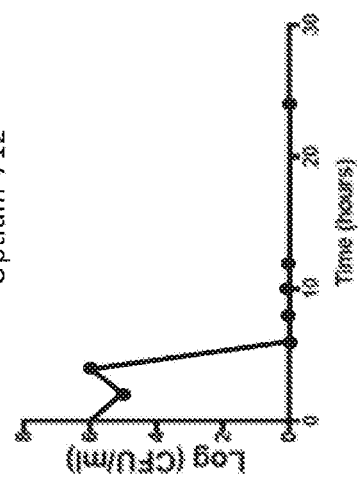
Figure 4C:
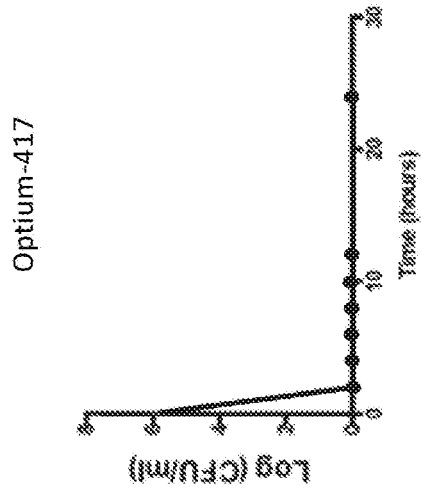
Figure 4D:
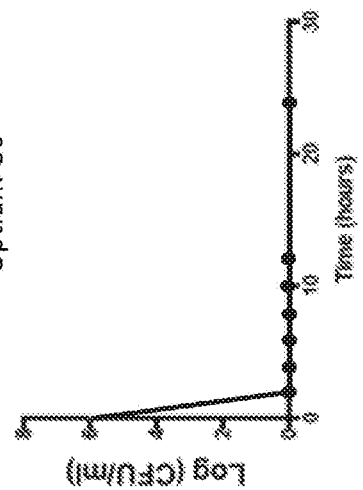
Figure 4E:
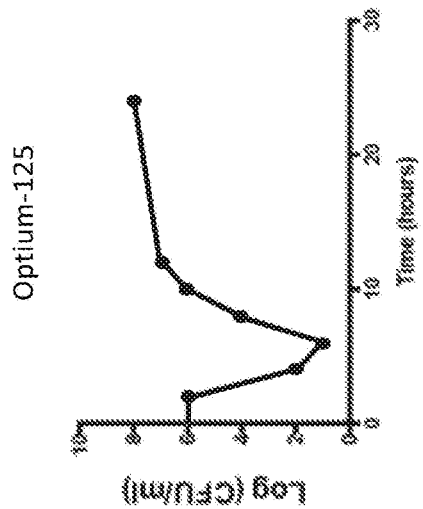
Figure 4F:
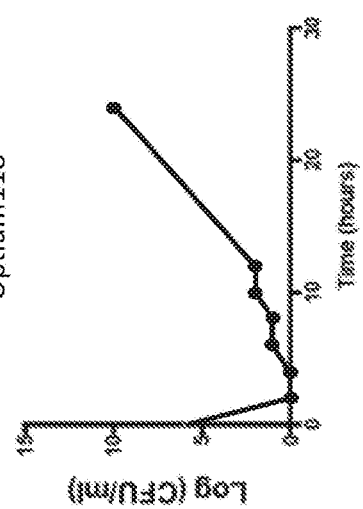
Figure 4I:
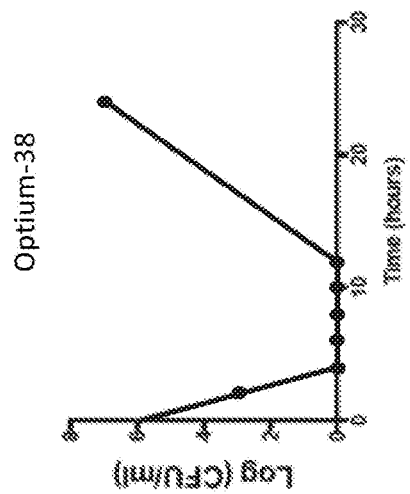
Figure 4H:
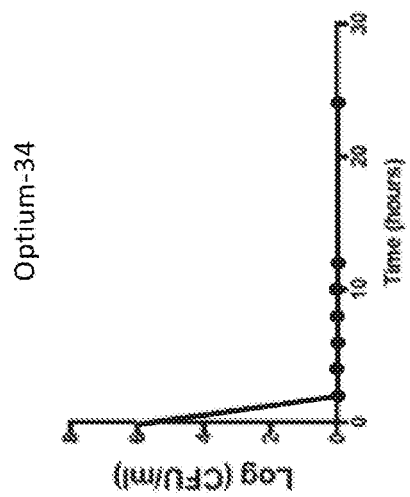
Figure 4G:
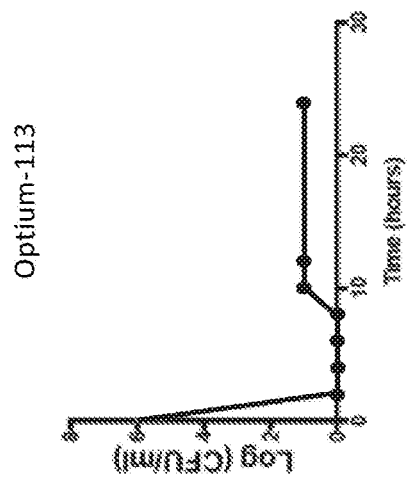

In particular, and as shown in FIG. 2A, there was a 20.8% average reduction in hsCRP in the seven participants whose hsCRP levels were above the normal healthy range before the four-week trial ($p=0.031$). As shown in FIG. 2B, there was a 14.6% average reduction in hsCRP levels across all participants. On average, there was a 1.4% reduction in body weight ($p=0.049$; FIG. 2C), a 1.8% reduction in BMI ($p=0.003$, FIG. 2D), and a 6.5% increase in HDL cholesterol ($p=0.013$, FIG. 2E).

Additionally, as shown in FIGS. 2F-2I, respectively, the trial group demonstrated a 2.4% decrease in fasting blood glucose levels, a 5.3% decrease in alanine aminotransferase (ALT), a 6.4% decrease in aspartate aminotransferase (AST), and a 6.7% decrease in triglycerides.

Daily tracking data recorded by participants further noted the following benefits and impacts associated with administration of the composition. Overall, 76% of participants felt a positive impact from use of the bacteriophage cocktail (24% neutral or negative), 59% reported higher energy and better stamina, 53% reported greater regularity and ease of bowel movements with softer stools (29% noted initial constipation during 1$^{st}$ week), 41% had less appetite, most notably in the afternoons, 29% experienced better muscle tone and/or reduced inches around arms and/or waist, 24% reported strong improvement in complexion/skin and reduced acne, 24% reported improved mood and better mental awareness, 18% were more able to concentrate and focus, 12% reported improvements in self-reported levels of depression (2 of 2 participants with depression noted this positive impact), and 12% experienced alleviation/elimination of chronic stomach aches.

Example 3

An exemplary method for identifying and characterizing bacteriophages for inclusion within a composition for reducing the number or concentration of a bacterium associated with the intestinal microbiome of a mammal includes at least the following method acts.

In general, the method can include: (1) collecting environment sample(s); (2) setting up enrichment culture; (3) isolating phage from the enrichment culture; (4) purifying the phage; (5) phage titer test to high concentration; (6) characterizing the phage (e.g., using electron microscope and genomic DNA isolation and sequencing); (7) performing a restriction enzyme assay; (8) performing a lytic activity assay; and (9) optionally preparing a phage frozen stock.

More particularly, the method can include collect an environment sample from the soil, sewage water, or other environmental source and setting up an enrichment culture. The enrichment culture can include, for example, 25 mL LB broth, 1 mL target bacterium, and 1 mL of the environment sample. The inoculated enrichment culture is then incubated (e.g., at 35° C. for 2 days with aeration). Following incubation, the liquid can be transferred from the flask into a cylindrical or conical tube for centrifugation (e.g., at 8000 RPM for 20 minutes). The supernatant can then be filtered (e.g., using a 0.45 μm filter) into another sterile conical tube and optionally refrigerated.

The phage can subsequently be isolated from the enrichment culture. For example, the filtered enrichment culture can be mixed and serially diluted (e.g., by factors of 10) to a final concentration of $1 \times 10^{-7}$ PFU/mL. An overnight culture of the target bacterium can then be inoculated into each tubes of the dilution series (e.g., using 500 μL of the bacterial culture). The inoculated tubes are then incubated at 35° C. for 40 minutes. Following incubation, each sample is mixed with 5 mL of melted top agar and plated (e.g., onto petri dishes). The plated samples are incubated for 24 h or until plaque formation is visible.

The phages are purified by picking a single plaque with a sterile needle and transferring to sterile media (e.g., LB broth). The inoculated media is mixed, incubated, and phages picked from a resulting plaque are filtered as before prior to serial dilution. An overnight culture of the target bacterium can then be inoculated into each tubes of the dilution series (e.g., using 500 μL of the bacterial culture). The inoculated tubes are then incubated at 35° C. for 40 minutes. Following incubation, each sample is mixed with 5 mL of melted top agar and plated (e.g., onto petri dishes). The plated samples are incubated for 24 h or until plaque formation is visible. This phage purification process may be repeated two or more times.

Following the purification step, the phage titer is determined. This can allow isolation of phage to an adequate high concentration in preparation for further analysis. The phage titer assay can be conducted, for example, by mixing 20 mL LB broth, 0.5 mL of an overnight culture of the target bacterium, and plaque picking from the last phage purification round that had been suspended in 100 uL LB broth. The flask is then incubated at 35° C. for 2 days with medium shaking. Following this incubation period, the sample is centrifuged (e.g., 8000 rpm for 10-15 minutes) and supernatant filtered (e.g., through a 0.45 μm filter). The filtered supernatant can then be used, as above, to generate plaques for determining the concentration of phage within the filtered lysate.

Preferably, the final concentration of the phage lysate is greater than or equal to $1 \times 10^8$ PFU/mL.

The phage can then be characterized. This includes isolating the phage DNA using methods and phage DNA isolation kits, as known in the art. The isolated phage DNA can be sequenced using any method or suitable technology known in the art. If characterized using electron microscopy, 10 μL of phage lysate is combined with 10 μL of tungsten heavy metal solution and placed on an electron microscopy grid and viewed via electron microscopy, as known in the art.

The electron microscopy data can be used to determine phage morphology and structural classification. The sequenced phage DNA can be used to confirm the lack of any bacterial toxin and/or virulence factor and/or integrase gene, and to compare with other phage DNA having a similar tropism for a relative genetic similarity.

Example 4

An exemplary method for determining lytic activity and tropism for identified bacteriophages includes at least the following method acts.

To identify lytic phages, a target bacterium, such as *Enterobacter cloacae* strain B29, was diluted from an overnight culture to a concentration of $1 \times 10^6$ colony-forming units per milliliter (CFU/mL) and inoculated with phage titered to a concentration of $1 \times 10^8$ PFU/mL, giving a multiplicity of infection of 100. One milliliter of sample was removed from the flask, serial diluted, spread over LB-agar plates, and incubated overnight. The number of surviving bacteria was determined by colony count the next day. An additional 1 mL of each sample was removed from respective cultures every 2 hours during the first 12 hours after inoculation then once more at the $24^{th}$ hour after inoculation to detect whether the phage was lytic and whether bacteria develop resistance within the first 24 hours.

The tropism, or target specificity, of each phage was tested by measuring its ability to lyse a range of bacteria, from closely to distantly related bacterial strains. For example, Table 3 illustrates host range testing of 9 bacteriophages that were initially isolated based on their ability to lyse *Enterobacter cloacae* strain B29. Each phage was tested against two other *E. cloacae* strains, namely ATCC 13047 and ATCC 23855, as well as more distantly related *Shigella boydii* (ATCC 9207), *Klebsiella pneumoniae* (ATCC 10031), *Salmonella enterica* Serovar *Typhimurium* LT2, *Escherichia coli* strain 814, *Serratia marcescens*, and *Pseudomonas aeruginosa*.

A spot test was performed by dropping 100 μL of the respective phage solution containing $1 \times 10^9$ PFU/mL onto a lawn of specified-target bacterium and incubating overnight at 37° C. The results are illustrated in Table 3 where a positive indication corresponds to clearing of bacteria in the location where the phages were dropped or "spotted" on the plate. The clearance indicates lysis of the target bacterium and therefore tropism for the same. For example, as shown in Table 3, the different phages display tropism for different bacterial strains, while maintaining tropism for many (or all) of *Enterobacter cloacae* strains tested.

TABLE 3

Spot Test Results

| Species | Spot test | | | | | | | | |
|---|---|---|---|---|---|---|---|---|---|
| | Opt-38 | Opt-125 | Opt-417 | Opt-118 | Opt-34 | Opt-712 | Opt-113 | Opt-18 | Opt-86 |
| E. cloacae B29 | + | + | + | + | + | + | + | + | + |
| E. cloacae ATCC 13047 | + | + | + | + | + | + | + | + | + |
| E. cloacae ATCC 23855 | + | + | + | + | + | + | + | − | − |
| Shigella ATCC 9207 | − | − | − | − | − | − | − | − | − |
| Klebsiella ATCC 10031 | − | − | − | − | − | − | − | − | − |
| Salmonella LT2 | − | − | − | − | − | − | − | − | − |
| E. coli 814 | − | − | − | − | − | − | − | − | − |
| S. marcescnes | − | − | − | − | − | − | − | − | − |
| P. aeruginosa | + | − | − | − | − | − | − | − | − |

The lytic activity of the phages disclosed in Table 3 toward each vulnerable strain of bacteria was further quantified by mixing 100 µL of $1\times10^9$ PFU/mL phage with 500 µL of $1\times10^9$ CFU/mL bacteria and incubating overnight at 37° C. with shaking. The overnight cultures were serially diluted, plated, and plaques were enumerated on the incubated plates to assess each phage's ability to replicate in the host bacteria. Table 4 shows the results of said host range testing of the 9 bacteriophages of Table 3. As shown in Table 4, the different phages display tropisms specific for different strains of *Enterobacter cloacae* (and in one instance *P. aeruginosa*) and are capable of replicating within and lysing the different strains of *Enterobacter cloacae*.

TABLE 4

Infection Efficiency Results

| Species | Efficiency of plating (PFU/ml) | | | | |
|---|---|---|---|---|---|
| | Opt-38 | Opt-125 | Opt-417 | Opt-118 | Opt-34 |
| E. cloacae 629 | $1.77 \times 10^{11}$ | $3.88 \times 10^{11}$ | $2.31 \times 10^{110}$ | $3.31 \times 10^{111}$ | $2.87 \times 10^{8}$ |
| E. cloacae ATCC 13047 | $3.78 \times 10^{10}$ | $2.12 \times 10^{10}$ | $5.55 \times 10^{7}$ | $1.12 \times 10^{113}$ | $4.68 \times 10^{11}$ |
| E. cloacae ATCC 23855 | $1.33 \times 10^{7}$ | $1.44 \times 10^{8}$ | $1.722 \times 10^{14}$ | $8.22 \times 10^{15}$ | $3.33 \times 10^{8}$ |
| Shigella ATCC 9207 | ND | ND | ND | ND | ND |
| Klebsiella ATCC 10031 | ND | ND | ND | ND | ND |
| Salmonella LT2 | ND | ND | ND | ND | ND |
| E. coli 814 | ND | ND | ND | ND | ND |
| S. marcescnes | ND | ND | ND | ND | ND |
| P. aeruginosa | $1.38 \times 10^{7}$ | ND | ND | ND | ND |

| Species | Efficiency of plating (PFU/ml) | | | |
|---|---|---|---|---|
| | Opt-712 | Opt-113 | Opt-18 | Opt-86 |
| E. cloacae 629 | $5.55 \times 10^{7}$ | $6.13 \times 10^{8}$ | $7.46 \times 10^{10}$ | $1.27 \times 10^{11}$ |
| E. cloacae ATCC 13047 | $4.81 \times 10^{8}$ | $1.16 \times 10^{9}$ | $1.68 \times 10^{11}$ | $1.58 \times 10^{13}$ |
| E. cloacae ATCC 23855 | $2.22 \times 10^{5}$ | $2.44 \times 10^{7}$ | ND | $5.01 \times 10^{8}$ |
| Shigella ATCC 9207 | ND | ND | ND | ND |
| Klebsiella ATCC 10031 | ND | ND | ND | ND |
| Salmonella LT2 | ND | ND | ND | ND |
| E. coli 814 | ND | ND | ND | ND |
| S. marcescnes | ND | ND | ND | ND |
| P. aeruginosa | ND | ND | ND | ND |

Example 5

In order for identified phages to be considered for inclusion in the disclosed compositions, we demonstrated that each phage can survive conditions in the mammalian gastrointestinal tract. Phage cocktails were administered to mice by oral gavage, followed by fecal sample collection from which the concentration of phage could be measured. Phages shown by these tests to survive the digestive tract were considered for subsequent development of a therapeutic cocktail.

In particular, for each phage to be tested, male C57 mice (6 weeks old) were obtained and divided into negative control (n=3) and test groups (n=7). The control group were given 0.2 mL sterile Luria broth (LB) via oral gavage once. Test groups were given $1\times10^{10}$ PFU/mL of phage in 0.2 mL of LB broth via oral gavage once. Phages were grown in and purified from host bacteria, and titer determined by standard plaque assay before diluting the phage to the stated concentration in LB. Immediately before the oral gavage, fecal samples were collected from all mice. Fecal samples were also collected from all mice every 6 hours until the 24th hour after gavage. Immediately after collection, each fecal sample was resuspended in phosphate buffered saline and filtered through a 0.45 μm filter to isolate phage. The filtered solution was grown with host bacteria in a standard plaque-forming assay to calculate phage concentration in the fecal sample and thus determine how well the phage had survived the digestive tract. Table 5 shows survivability of the 9 bacteriophages disclosed in Tables 3 and 4 above after passage through the mouse gastrointestinal tract. As shown in Table 1, the different phages are capable of surviving within the digestive tract for an extended period of time.

TABLE 5

Gut Survivability Test Results

| Phages: | Gut Survivalbility Test: Time (hrs) | | | |
|---|---|---|---|---|
| | 0 | 6 | 12 | 24 |
| Opt-38 | − | + | + | + |
| Opt-125 | − | + | + | + |
| Opt-417 | − | + | + | + |
| Opt-118 | − | + | + | + |
| Opt-34 | − | + | + | + |
| Opt-712 | − | + | + | + |
| Opt-113 | − | + | + | + |
| Opt-18 | − | + | + | + |
| Opt-86 | − | + | + | + |

Example 6

In vivo proof-of-principle testing was performed to determine whether phage treatment of gut-associated *Enterobacter cloacae* strain B29 can reduce obesity, inflammation, or other associated metabolic disorders in an animal model. Germ-free mice were inoculated orally with *E. cloacae* strain B29, which was shown to cause inflammation and obesity in the mice. Mice were treated by oral administration of phage tropic for *E. cloacae* strain B29. Phages were tested individually and in combinations of two or more phages, to determine whether inflammation or obesity decreased and to guide formulation of a cocktail to which obesogenic bacteria are unlikely to develop resistance owing at least in part to the multiple phages that are not closely related to each other.

Using broad-spectrum antibiotics to first deplete the native mouse gut microbiota so that *Enterobacter cloacae* strain B29, which does not normally colonize mice, engrafts. Nine bacteriophages with a narrow tropism that includes *Enterobacter cloacae* strain B29 were isolated, verified as lytic, and shown to survive conditions in the mammalian gastrointestinal (GI) tract. Multiple phages that attack their target through different surface receptors were used to decrease the likelihood that target bacteria would evolve resistance to infection.

Figure 5:
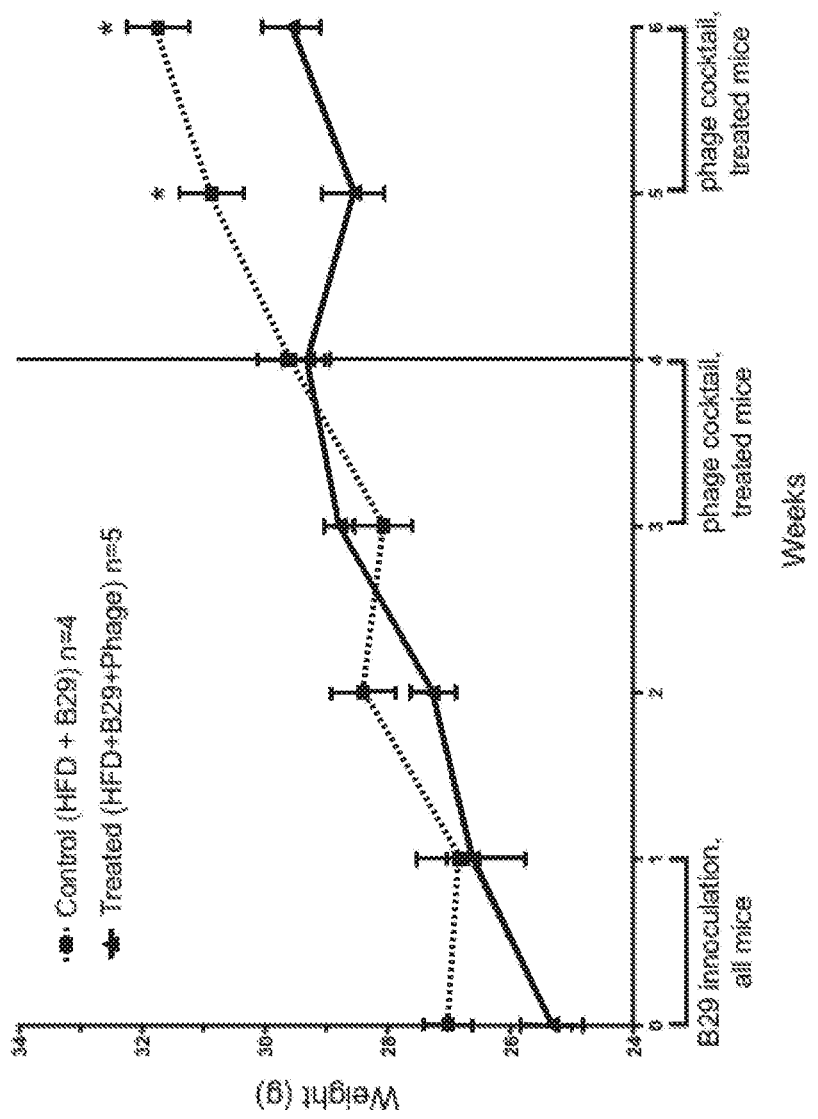
FIG. 5 illustrates a graphical representation showing arrested weight gain in mice with intestinal microbiomes colonized with *Enterobacter cloacae* strain B29 that are treated with *E. cloacae* tropic bacteriophages as compared to untreated control mice with intestinal microbiomes colonized with *Enterobacter cloacae* strain B29.

FIG. 5 is a graphical representation showing arrest of weight gain in mice colonized with *Enterobacter cloacae* strain B29 and subsequently treated with bacteriophages as compared to control mice with intestinal microbiomes colonized with *Enterobacter cloacae* strain B29 but untreated with bacteriophage. As shown in FIG. 5, the administered phage cocktail inhibited *E. cloacae* strain B29-induced weight gain.

During week 1 of the in vivo study, all mice received daily doses of *E. cloacae* strain B29 by oral gavage and were placed on a high fat diet to induce weight gain. At week 3, the treatment group (solid line with triangles) received daily doses of the phage cocktail by oral gavage for 7 days. The phage treatment was repeated at week 5. Body weight was monitored weekly throughout the study and was shown to be significantly different in the phage-treated group as compared to the control group at weeks 5 and 6 ($p<0.05$).

The study included 6 groups of 8 mice each. The study groups included:

Group 1: Obese control: mice with normal gut microbiota; developed obesity.

Group 2: Lean control: mice with antibiotic-depleted gut microbiota; did not develop obesity.

Group 3: Obese control #2: mice with antibiotic-depleted gut microbiota inoculated with *E. cloacae* strain B29 to reconstitute gut microbiota; developed obesity.

Group 4: Experimental Group #1: mice administered phage cocktail at beginning of week 3 during antibiotic-depletion, one week prior to first inoculation with *E. cloacae* strain B29; administration of phage cocktail correlates with prevention of *E. cloacae* strain B29 engraftment and prevented development of obesity.

Group 5: Experimental Group #2: mice administered phage cocktail at the beginning of week 7 after *E. cloacae* strain B29 had engrafted but before obesity developed; phage treatment correlated with prevented development of obesity, reduced *E. cloacae* strain B29 levels, and reduced inflammation.

Group 6: Experimental Group #3: mice administer phage cocktail at the beginning of week 17 after obesity had developed; phage administration correlated with decreased low-level systemic inflammation, weight loss, and reduction of *E. cloacae* strain B29 levels in the mouse gut microbiome.

The study was designed to measure the efficacy of phage treatment when administered before exposure to *E. cloacae* strain B29, after exposure to *E. cloacae* strain B29 but before obesity develops, and after obesity develops due to colonization of *E. cloacae* strain B29 within the mouse gut microbiota. Broad-spectrum antibiotics were administered to Groups 2-6 (see group descriptions above) to deplete their native gut microbiota during weeks 1-3, then their microbiotas were reconstituted (except group 2) by twice-daily oral gavage with $1\times10^{10}$ CFU/mL of *E. cloacae* strain B29 during week 4. All mice were fed a high fat diet at the start of week 5 and remained on that diet for the duration of the study.

The methods for antibiotic depletion and *E. cloacae* strain B29 reconstitution of the gut microbiota were tested and proven effective. When the *E. cloacae* strain B29 levels decreased in Group 3 controls during the study, a biweekly "booster" dose of *E. cloacae* strain B29 was administered to groups 3-6. Bodyweight was measured weekly throughout the study. Phage treatments were initiated at the time points indicated and administered by daily oral gavage for the first week of treatment, then by inclusion in drinking water for the duration of the study.

Fecal samples were collected and cultured biweekly beginning at the end of week 4 to track *E. cloacae* strain B29 levels. Glucose tolerance and insulin sensitivity were measured every 4 weeks (as described below) to detect type 2 diabetes. By week 12, we demonstrated obesity in control mice. By week 24, conclusions regarding the effect of the *E. cloacae* strain B29 phage cocktail on body weight and glucose tolerance when given before *E. cloacae* strain B29 exposure, after *E. cloacae* strain B29 engraftment but before obesity developed, or after *E. cloacae* strain B29 engraftment and after obesity were established.

Molecular Level Analyses of Mouse Tissues for Markers of Inflammation and Insulin Resistance Each mouse was dissected at the end of the study and various tissues were preserved. Molecular markers of inflammation such as tumor necrosis factor α (TNF-α), interleukin 1β interleukin (IL-6), toll like receptor 4 (TLR-4), and I-kappa-B kinase epsilon (IKKε) were examined in liver, intestine, and adipose tissue using qRT-PCR. ELISA assays were used to measure serum levels of proteins that influence blood sugar and appetite (e.g., insulin, leptin, and adiponectin), and inflammation (e.g., serum amyloid A and LPS-binding protein).

Some or all molecular markers of inflammation and glucose dysregulation improved in response to the administration of the phage cocktail to mice harboring *E. cloacae* strain B29. Additional markers of insulin activity (e.g., AccI, Fas, Fiaf, Srebp1, Pparq) and gut permeability (ZO-1, Occludin, Claudin) were examined at the RNA and protein levels in tissues. The mechanisms underlying bodyweight changes were deduced by quantification of the molecular-level changes that occurred in mice in response to administration of the phage cocktail.

CONCLUSION

It will be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Likewise, any steps recited in any method or process described herein and/or recited in the claims can be executed in any suitable order and are not necessarily limited to the order described and/or recited, unless otherwise stated (explicitly or implicitly). Such steps can, however, also be performed in a specific order or any suitable order in certain embodiments of the present disclosure.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the compositions and kits disclosed herein may be made without departing from the scope of the disclosure or of the invention, which is defined in the appended claims. All changes which come within the meaning and range of equivalency of the claims are to be embraced within their scope.

The Sequence Listing accompanying the present disclosure and submitted herewith forms a part of the present disclosure and is incorporated herein by specific reference.

SEQUENCE LISTING

The patent contains a lengthy sequence listing. A copy of the sequence listing is available in electronic form from the USPTO web site (https://seqdata.uspto.gov/?pageRequest=docDetail&DocID=US11986502B2). An electronic copy of the sequence listing will also be available from the USPTO upon request and payment of the fee set forth in 37 CFR 1.19(b)(3).

What is claimed is:

1. A composition, comprising:
a pharmaceutically-acceptable carrier; and
greater than or equal to $1 \times 10^4$ PFU of each of a plurality of bacteriophages, the plurality of bacteriophages comprising:
a first bacteriophage having a genome with greater than or equal to 80% sequence identity to a first one of SEQ ID NO:2, SEQ ID NO:3, SEQ ID NO:5, or SEQ ID NO:6;
a second bacteriophage having a genome with greater than or equal to 80% sequence identity to a second one of SEQ ID NO:2, SEQ ID NO:3, SEQ ID NO:5, or SEQ ID NO:6;
a third bacteriophage having a genome with greater than or equal to 80% sequence identity to a first one of SEQ ID NO:1, SEQ ID NO:4, SEQ ID NO:10, or SEQ ID NO:14;
a fourth bacteriophage having a genome with greater than or equal to 80% sequence identity to a second one of SEQ ID NO:1, SEQ ID NO:4, SEQ ID NO:10, or SEQ ID NO:14;
a fifth bacteriophage having a genome with greater than or equal to 80% sequence identity to a first one of SEQ ID NO:7, SEQ ID NO:8, or SEQ ID NO:9;
a sixth bacteriophage having a genome with greater than or equal to 80% sequence identity to a second one of SEQ ID NO:7, SEQ ID NO:8, or SEQ ID NO:9;
a seventh bacteriophage having a genome with greater than or equal to 80% sequence identity to a first one of SEQ ID NO:12, nucleic acid bases 1-59,985 of SEQ ID NO:13, or SEQ ID NO:15; and
an eighth bacteriophage having a genome with greater than or equal to 80% sequence identity to a second one of SEQ ID NO:12, nucleic acid bases 1-59,985 of SEQ ID NO:13, or SEQ ID NO:15.

2. The composition of claim 1, wherein the first bacteriophage has a genome with greater than or equal to 90% sequence identity to the first one of SEQ ID NO:2, SEQ ID NO:3, SEQ ID NO:5, or SEQ ID NO:6 and wherein the second bacteriophage has a genome with greater than or equal to 90% sequence identity to the second one of SEQ ID NO:2, SEQ ID NO:3, SEQ ID NO:5, or SEQ ID NO:6.

3. The composition of claim 1, wherein one or more of the plurality of bacteriophages is present at greater than or equal to $1 \times 10^8$ PFU.

4. The composition of claim 1, wherein:
the first bacteriophage has a genome with greater than or equal to 90% sequence identity to the first one of SEQ ID NO:2, SEQ ID NO:3, SEQ ID NO:5, or SEQ ID NO:6; and
the second bacteriophage has a genome with greater than or equal to 90% sequence identity to the second one of SEQ ID NO:2, SEQ ID NO:3, SEQ ID NO:5, or SEQ ID NO:6;
the third bacteriophage has a genome with greater than or equal to 90% sequence identity to the first one of SEQ ID NO:1, SEQ ID NO:4, SEQ ID NO:10, or SEQ ID NO:14;
the fourth bacteriophage has a genome with greater than or equal to 90% sequence identity to the second one of SEQ ID NO:1, SEQ ID NO:4, SEQ ID NO:10, or SEQ ID NO:14;
the fifth bacteriophage has a genome with greater than or equal to 90% sequence identity to a first one of SEQ ID NO:7, SEQ ID NO:8, or SEQ ID NO:9;
the sixth bacteriophage has a genome with greater than or equal to 90% sequence identity to the second one of SEQ ID NO:7, SEQ ID NO:8, or SEQ ID NO:9;
the seventh bacteriophage has a genome with greater than or equal to 90% sequence identity to a first one of SEQ ID NO:12, nucleic acid bases 1-59,985 of SEQ ID NO:13, or SEQ ID NO:15; and
the eighth bacteriophage has a genome with greater than or equal to 90% sequence identity to the second one of SEQ ID NO:12, nucleic acid bases 1-59,985 of SEQ ID NO:13, or SEQ ID NO:15.

5. A composition, comprising:
a pharmaceutically-acceptable carrier; and
greater than or equal to $1 \times 10^4$ PFU of each of a plurality of bacteriophages, the plurality of bacteriophages comprising:
a first bacteriophage having a genome with a first tropic element having greater than or equal to 80% sequence identity to a tropic element of a first one of SEQ ID NO:2, SEQ ID NO:3, SEQ ID NO:5, or SEQ ID NO:6;
a second bacteriophage having a genome with a second tropic element having greater than or equal to 80% sequence identity to a tropic element of a second one of SEQ ID NO:2, SEQ ID NO:3, SEQ ID NO:5, or SEQ ID NO:6;
a third bacteriophage having a genome with a third tropic element having greater than or equal to 80% sequence identity to a tropic element of a first one of SEQ ID NO:1, SEQ ID NO:4, SEQ ID NO:10, or SEQ ID NO:14;
a fourth bacteriophage having a genome with a fourth tropic element having greater than or equal to 80% sequence identity to a tropic element of a second one of SEQ ID NO:1, SEQ ID NO:4, SEQ ID NO:10, or SEQ ID NO:14;
a fifth bacteriophage having a genome with a fifth tropic element having greater than or equal to 80% sequence identity to a tropic element of a first one of SEQ ID NO:7, SEQ ID NO:8, or SEQ ID NO:9;
a sixth bacteriophage having a genome with a sixth tropic element having greater than or equal to 80% sequence identity to a tropic element of a second one of SEQ ID NO:7, SEQ ID NO:8, or SEQ ID NO:9;
a seventh bacteriophage having a genome a seventh tropic element having with greater than or equal to 80% sequence identity to a tropic element of a first one of SEQ ID NO:12, nucleic acid bases 1-59,985 of SEQ ID NO:13, or SEQ ID NO:15; and
an eighth bacteriophage having a genome with an eighth tropic element having greater than or equal to 80% sequence identity to a tropic element of a second one of SEQ ID NO:12, nucleic acid bases 1-59,985 of SEQ ID NO:13, or SEQ ID NO:15.

6. The composition of claim 5, wherein:
the first tropic element has greater than or equal to 90% sequence identity to the tropic element of the first one of SEQ ID NO:2, SEQ ID NO:3, SEQ ID NO:5, or SEQ ID NO:6; and
the second tropic element has greater than or equal to 90% sequence identity to the tropic element of the second one of SEQ ID NO:2, SEQ ID NO:3, SEQ ID NO:5, or SEQ ID NO:6.

7. The composition of claim 5, wherein:
the first tropic element has greater than or equal to 90% sequence identity to the tropic element of the first one of SEQ ID NO:2, SEQ ID NO:3, SEQ ID NO:5, or SEQ ID NO:6;
the second tropic element has greater than or equal to 90% sequence identity to the tropic element of the second one of SEQ ID NO:2, SEQ ID NO:3, SEQ ID NO:5, or SEQ ID NO:6;
the third tropic element has greater than or equal to 90% sequence identity to the tropic element of the first one of SEQ ID NO:1, SEQ ID NO:4, SEQ ID NO:10, or SEQ ID NO:14;
the fourth tropic element has greater than or equal to 90% sequence identity to the tropic element of the second one of SEQ ID NO:1, SEQ ID NO:4, SEQ ID NO:10, or SEQ ID NO:14;
the fifth tropic element has greater than or equal to 90% sequence identity to the tropic element of the first one of SEQ ID NO:7, SEQ ID NO:8, or SEQ ID NO:9;
the sixth tropic element has greater than or equal to 90% sequence identity to the tropic element of the second one of SEQ ID NO:7, SEQ ID NO:8, or SEQ ID NO:9;
the seventh tropic element has greater than or equal to 90% sequence identity to the tropic element of the first one of SEQ ID NO:12, nucleic acid bases 1-59,985 of SEQ ID NO:13, or SEQ ID NO:15; and
the eighth tropic element has greater than or equal to 90% sequence identity to the tropic element of the second one of SEQ ID NO:12, nucleic acid bases 1-59,985 of SEQ ID NO:13, or SEQ ID NO:15.

8. The composition of claim 5, one or more of the plurality of bacteriophages is present at greater than or equal to $1 \times 10^8$ PFU.

9. The composition of claim 5, wherein the plurality of bacteriophages comprises at least 14 different bacteriophages having respective genomes each with a tropic element having greater than or equal to 80% sequence identity to a respective tropic element of SEQ ID NO:2, SEQ ID NO:3, SEQ ID NO:5, SEQ ID NO:6, SEQ ID NO:1, SEQ ID NO:4, SEQ ID NO:10, SEQ ID NO:14, SEQ ID NO:7, SEQ ID NO:8, SEQ ID NO:9, SEQ ID NO:12, nucleic acid bases 1-59,985 of SEQ ID NO:13, and SEQ ID NO:15.

10. The composition of claim 5, wherein the plurality of bacteriophages comprises at least 14 different bacteriophages having respective genomes each with a tropic element having greater than or equal to 85% sequence identity to a respective tropic element of SEQ ID NO:2, SEQ ID NO:3, SEQ ID NO:5, SEQ ID NO:6, SEQ ID NO:1, SEQ ID NO:4, SEQ ID NO:10, SEQ ID NO:14, SEQ ID NO:7, SEQ ID NO:8, SEQ ID NO:9, SEQ ID NO:12, nucleic acid bases 1-59,985 of SEQ ID NO:13, and SEQ ID NO:15.

11. The composition of claim 5, wherein the plurality of bacteriophages comprises at least 14 different bacteriophages having respective genomes each with a tropic element having greater than or equal to 90% sequence identity to a respective tropic element of SEQ ID NO:2, SEQ ID NO:3, SEQ ID NO:5, SEQ ID NO:6, SEQ ID NO:1, SEQ ID NO:4, SEQ ID NO:10, SEQ ID NO:14, SEQ ID NO:7, SEQ ID NO:8, SEQ ID NO:9, SEQ ID NO:12, nucleic acid bases 1-59,985 of SEQ ID NO:13, and SEQ ID NO:15.

12. The composition of claim 1, wherein the plurality of bacteriophages comprises at least 14 different bacteriophages having respective genomes each with greater than or equal to 80% sequence identity to a respective one of SEQ ID NO:2, SEQ ID NO:3, SEQ ID NO:5, SEQ ID NO:6, SEQ ID NO:1, SEQ ID NO:4, SEQ ID NO:10, SEQ ID NO:14, SEQ ID NO:7, SEQ ID NO:8, SEQ ID NO:9, SEQ ID NO:12, nucleic acid bases 1-59,985 of SEQ ID NO:13, and SEQ ID NO:15.

13. The composition of claim 1, wherein the plurality of bacteriophages comprises at least 14 different bacteriophages having respective genomes each with greater than or equal to 85% sequence identity to a respective one of SEQ ID NO:2, SEQ ID NO:3, SEQ ID NO:5, SEQ ID NO:6, SEQ ID NO:1, SEQ ID NO:4, SEQ ID NO:10, SEQ ID NO:14, SEQ ID NO:7, SEQ ID NO:8, SEQ ID NO:9, SEQ ID NO:12, nucleic acid bases 1-59,985 of SEQ ID NO:13, and SEQ ID NO:15.

14. The composition of claim 1, wherein the plurality of bacteriophages comprises at least 14 different bacteriophages having respective genomes each with greater than or equal to 90% sequence identity to a respective one of SEQ ID NO:2, SEQ ID NO:3, SEQ ID NO:5, SEQ ID NO:6, SEQ ID NO:1, SEQ ID NO:4, SEQ ID NO:10, SEQ ID NO:14, SEQ ID NO:7, SEQ ID NO:8, SEQ ID NO:9, SEQ ID NO:12, nucleic acid bases 1-59,985 of SEQ ID NO:13, and SEQ ID NO:15.

15. A composition, comprising:
  a pharmaceutically-acceptable carrier; and
  greater than or equal to $1\times10^4$ PFU of each of a plurality of bacteriophages, the plurality of bacteriophages comprising:
    a first bacteriophage having a genome with a first tropic element having greater than or equal to 80% sequence identity to a tropic element of a first one of SEQ ID NO:2, SEQ ID NO:3, SEQ ID NO:5, or SEQ ID NO:6;
    a second bacteriophage having a genome with a second tropic element having greater than or equal to 80% sequence identity to a tropic element of a second one of SEQ ID NO:2, SEQ ID NO:3, SEQ ID NO:5, or SEQ ID NO:6;
    a third bacteriophage having a genome with a third tropic element having greater than or equal to 80% sequence identity to a tropic element of a first one of SEQ ID NO:1, SEQ ID NO:4, SEQ ID NO:10, or SEQ ID NO:14;
    a fourth bacteriophage having a genome with a fourth tropic element having greater than or equal to 80% sequence identity to a tropic element of a second one of SEQ ID NO:1, SEQ ID NO:4, SEQ ID NO:10, or SEQ ID NO:14; and
    at least one pair of bacteriophage selected from the group consisting of:
      (i) a fifth bacteriophage having a genome with a fifth tropic element having greater than or equal to 80% sequence identity to a tropic element of a first one of SEQ ID NO:7, SEQ ID NO:8, or SEQ ID NO:9; and
      a sixth bacteriophage having a genome with a sixth tropic element having greater than or equal to 80% sequence identity to a tropic element of a second one of SEQ ID NO:7, SEQ ID NO:8, or SEQ ID NO:9; and
      (ii) a seventh bacteriophage having a genome a seventh tropic element having with greater than or equal to 80% sequence identity to a tropic element of a first one of SEQ ID NO:12, nucleic acid bases 1-59,985 of SEQ ID NO:13, or SEQ ID NO:15; and
      an eighth bacteriophage having a genome with an eighth tropic element having greater than or equal to 80% sequence identity to a tropic element of a second one of SEQ ID NO:12, nucleic acid bases 1-59,985 of SEQ ID NO:13, or SEQ ID NO:15.

16. The composition of claim 15, wherein the at least one pair of bacteriophage comprises the fifth bacteriophage and the sixth bacteriophage, and wherein:
  the first tropic element has greater than or equal to 85% sequence identity to the tropic element of the first one of SEQ ID NO:2, SEQ ID NO:3, SEQ ID NO:5, or SEQ ID NO:6;
  the second tropic element has greater than or equal to 85% sequence identity to the tropic element of the second one of SEQ ID NO:2, SEQ ID NO:3, SEQ ID NO:5, or SEQ ID NO:6;
  the third tropic element has greater than or equal to 85% sequence identity to the tropic element of the first one of SEQ ID NO:1, SEQ ID NO:4, SEQ ID NO:10, or SEQ ID NO:14;
  the fourth tropic element has greater than or equal to 85% sequence identity to the tropic element of the second one of SEQ ID NO:1, SEQ ID NO:4, SEQ ID NO:10, or SEQ ID NO:14;
  the fifth tropic element has greater than or equal to 85% sequence identity to the tropic element of the first one of SEQ ID NO:7, SEQ ID NO:8, or SEQ ID NO:9; and
  the sixth tropic element has greater than or equal to 85% sequence identity to the tropic element of the second one of SEQ ID NO:7, SEQ ID NO:8, or SEQ ID NO:9.

17. The composition of claim 15, wherein the at least one pair of bacteriophage comprises the fifth bacteriophage and the sixth bacteriophage, and wherein:
  the first tropic element has greater than or equal to 90% sequence identity to the tropic element of the first one of SEQ ID NO:2, SEQ ID NO:3, SEQ ID NO:5, or SEQ ID NO:6;
  the second tropic element has greater than or equal to 90% sequence identity to the tropic element of the second one of SEQ ID NO:2, SEQ ID NO:3, SEQ ID NO:5, or SEQ ID NO:6;
  the third tropic element has greater than or equal to 90% sequence identity to the tropic element of the first one of SEQ ID NO:1, SEQ ID NO:4, SEQ ID NO:10, or SEQ ID NO:14;
  the fourth tropic element has greater than or equal to 90% sequence identity to the tropic element of the second one of SEQ ID NO:1, SEQ ID NO:4, SEQ ID NO:10, or SEQ ID NO:14;
  the fifth tropic element has greater than or equal to 90% sequence identity to the tropic element of the first one of SEQ ID NO:7, SEQ ID NO:8, or SEQ ID NO:9; and the sixth tropic element has greater than or equal to 90% sequence identity to the tropic element of the second one of SEQ ID NO:7, SEQ ID NO:8, or SEQ ID NO:9.

18. The composition of claim 15, wherein the at least one pair of bacteriophage comprises the seventh bacteriophage and the eighth bacteriophage, and wherein:
   the first tropic element has greater than or equal to 85% sequence identity to the tropic element of the first one of SEQ ID NO:2, SEQ ID NO:3, SEQ ID NO:5, or SEQ ID NO:6;
   the second tropic element has greater than or equal to 85% sequence identity to the tropic element of the second one of SEQ ID NO:2, SEQ ID NO:3, SEQ ID NO:5, or SEQ ID NO:6;
   the third tropic element has greater than or equal to 85% sequence identity to the tropic element of the first one of SEQ ID NO:1, SEQ ID NO:4, SEQ ID NO:10, or SEQ ID NO:14;
   the fourth tropic element has greater than or equal to 85% sequence identity to the tropic element of the second one of SEQ ID NO:1, SEQ ID NO:4, SEQ ID NO:10, or SEQ ID NO:14;
   the seventh tropic element has greater than or equal to 85% sequence identity to the tropic element of the first one of SEQ ID NO:12, nucleic acid bases 1-59,985 of SEQ ID NO:13, or SEQ ID NO:15; and
   the eighth tropic element has greater than or equal to 85% sequence identity to the tropic element of the second one of SEQ ID NO:12, nucleic acid bases 1-59,985 of SEQ ID NO:13, or SEQ ID NO:15.

19. The composition of claim 15, wherein the at least one pair of bacteriophage comprises the seventh bacteriophage and the eighth bacteriophage, and wherein:
   the first tropic element has greater than or equal to 90% sequence identity to the tropic element of the first one of SEQ ID NO:2, SEQ ID NO:3, SEQ ID NO:5, or SEQ ID NO:6;
   the second tropic element has greater than or equal to 90% sequence identity to the tropic element of the second one of SEQ ID NO:2, SEQ ID NO:3, SEQ ID NO:5, or SEQ ID NO:6;
   the third tropic element has greater than or equal to 90% sequence identity to the tropic element of the first one of SEQ ID NO:1, SEQ ID NO:4, SEQ ID NO:10, or SEQ ID NO:14;
   the fourth tropic element has greater than or equal to 90% sequence identity to the tropic element of the second one of SEQ ID NO:1, SEQ ID NO:4, SEQ ID NO:10, or SEQ ID NO:14;
   the seventh tropic element has greater than or equal to 90% sequence identity to the tropic element of the first one of SEQ ID NO:12, nucleic acid bases 1-59,985 of SEQ ID NO:13, or SEQ ID NO:15; and
   the eighth tropic element has greater than or equal to 90% sequence identity to the tropic element of the second one of SEQ ID NO:12, nucleic acid bases 1-59,985 of SEQ ID NO:13, or SEQ ID NO:15.

20. The composition of claim 15, wherein one or more of the plurality of bacteriophages is present at greater than or equal to $1 \times 10^8$ PFU.

* * * * *